(12) United States Patent
Lum et al.

(10) Patent No.: US 9,783,550 B2
(45) Date of Patent: Oct. 10, 2017

(54) HIGHLY POTENT INHIBITORS OF PORCUPINE

(71) Applicant: The Board of Regents of the University of Texas System, Austin, TX (US)

(72) Inventors: Lawrence Lum, Dallas, TX (US); Chuo Chen, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/890,905

(22) PCT Filed: May 14, 2014

(86) PCT No.: PCT/US2014/037980
§ 371 (c)(1),
(2) Date: Nov. 12, 2015

(87) PCT Pub. No.: WO2014/186450
PCT Pub. Date: Nov. 20, 2014

(65) Prior Publication Data
US 2016/0115177 A1    Apr. 28, 2016

Related U.S. Application Data

(60) Provisional application No. 61/823,209, filed on May 14, 2013.

(51) Int. Cl.
| A61K 31/33 | (2006.01) |
| C07D 495/04 | (2006.01) |
| A61K 31/519 | (2006.01) |
| A61K 45/06 | (2006.01) |
| A61N 5/10 | (2006.01) |

(52) U.S. Cl.
CPC .......... *C07D 495/04* (2013.01); *A61K 31/519* (2013.01); *A61K 45/06* (2013.01); *A61N 5/10* (2013.01)

(58) Field of Classification Search
None
See application file for complete search history.

(56) References Cited

U.S. PATENT DOCUMENTS

| 2009/0163545 A1 | 6/2009 | Goldfarb |
| 2011/0136813 A1 | 6/2011 | Lum et al. |

FOREIGN PATENT DOCUMENTS

| WO | WO 2009-155001 | 12/2009 |
| WO | WO 2010-114636 | 10/2010 |

OTHER PUBLICATIONS

Wang et al (J Med Chem 56:2700-2704, 2014—published Mar. 11, 2013).*
Bastakoty et al., "Temporary, systemic inhibition of the WNT/β-catenin pathway promotes regenerative cardiac repair following myocardial infarct," *Cell Stem Cells Regen Med*, 2(2): doi http://dx.doi.org/10.16966/2472-6990.111, 2016.
Chen et al., "Small molecule-mediated disruption of Wnt-dependent signaling in tissue regeneration and cancer," *Nat. Chem. Biol.*, 5:100-107 2009.
Dodge et al., "Diverse chemical scaffolds support direct inhibition of the membrane-bound O-acyltransferase porcupine," *The Journal of Biological Chemistry*, 287(27):23246-23254, 2012.
Huang and He, "Wnt/beta-catenin signaling: new (and old) players and new insights," *Curr. Opin. Cell Biol.*, 20(2):119-125, 2008.
Karner et al., "Tankyrase is necessary for canonical Wnt signaling during kidney development," *Dev. Dyn.*, 239:2014-2023, 2010.
Lu et al.,"Structure/activity relationship studies of small-molecule inhibitors of Wnt response," *Bioorg. Med. Chem. Lett.*, 19:3825-3827, 2009.
PCT International Preliminary Report on Patentability issued in International Application No. PCT/US2014/037980, mailed Nov. 26, 2015.
PCT International Search Report and Written Opinion issued in International Application No. PCT/US2014/037980, mailed Dec. 5, 2014.
PubChem Compound Summary for CID 22430808, located at https://pubchem.ncbi.nlm.nih.gov/compound/22430808?from=summary, created Dec. 5, 2007, retrieved on Nov. 6, 2014.
PubChem Compound Summary for CID 35199602, located at https://pubchem.ncbi.nlm.nih.gov/compound/35199602?from=summary, created May 29, 2009, retrieved on Nov. 6, 2014.
PubChem Compound Summary for CID F0612-0124, located at https://pubchem.ncbi.nlm.nih.gov/compound/4676619?from=summary#section=Top, created Sep. 16, 2005, retrieved on Nov. 6, 2014.
Ren et al., "Small molecule Wnt inhibitors enhance the efficiency of BMP-4-directed cardiac differentiation of human pluripotent stem cells," *J. Mol. Cell Cardiol.*, 51:280-287, 2011.
Sato et al., "Paneth cells constitute the niche for Lgr5 stem cells in intestinal crypts," *Nature*, 469:415-418, 2011.
ten Berge et al., "Embryonic stem cells require Wnt proteins to prevent differentiation to epiblast stem cells," *Nat. Cell Biol.*, 13:1070-1075, 2011.
Wang et al., "The development of highly potent inhibitors for porcupine," *J Med Chem*, 56(6):2700-2704, 2013.
Yang et al., "Identification of the acyltransferase that octanoylates ghrelin, an appetite-stimulating peptide hormone," *Cell*, 132:387-396, 2008.

* cited by examiner

*Primary Examiner* — Craig Ricci
(74) *Attorney, Agent, or Firm* — Parker Highlander PLLC

(57) ABSTRACT

The present invention generally relates to protein signalling. In particular, compounds that inhibit the Wnt protein signalling pathway are disclosed. Such compounds may be used in the treatment of Wnt protein signalling-related diseases and conditions such as cancer, degenerative diseases, type II diabetes and osteopetrosis.

19 Claims, 15 Drawing Sheets

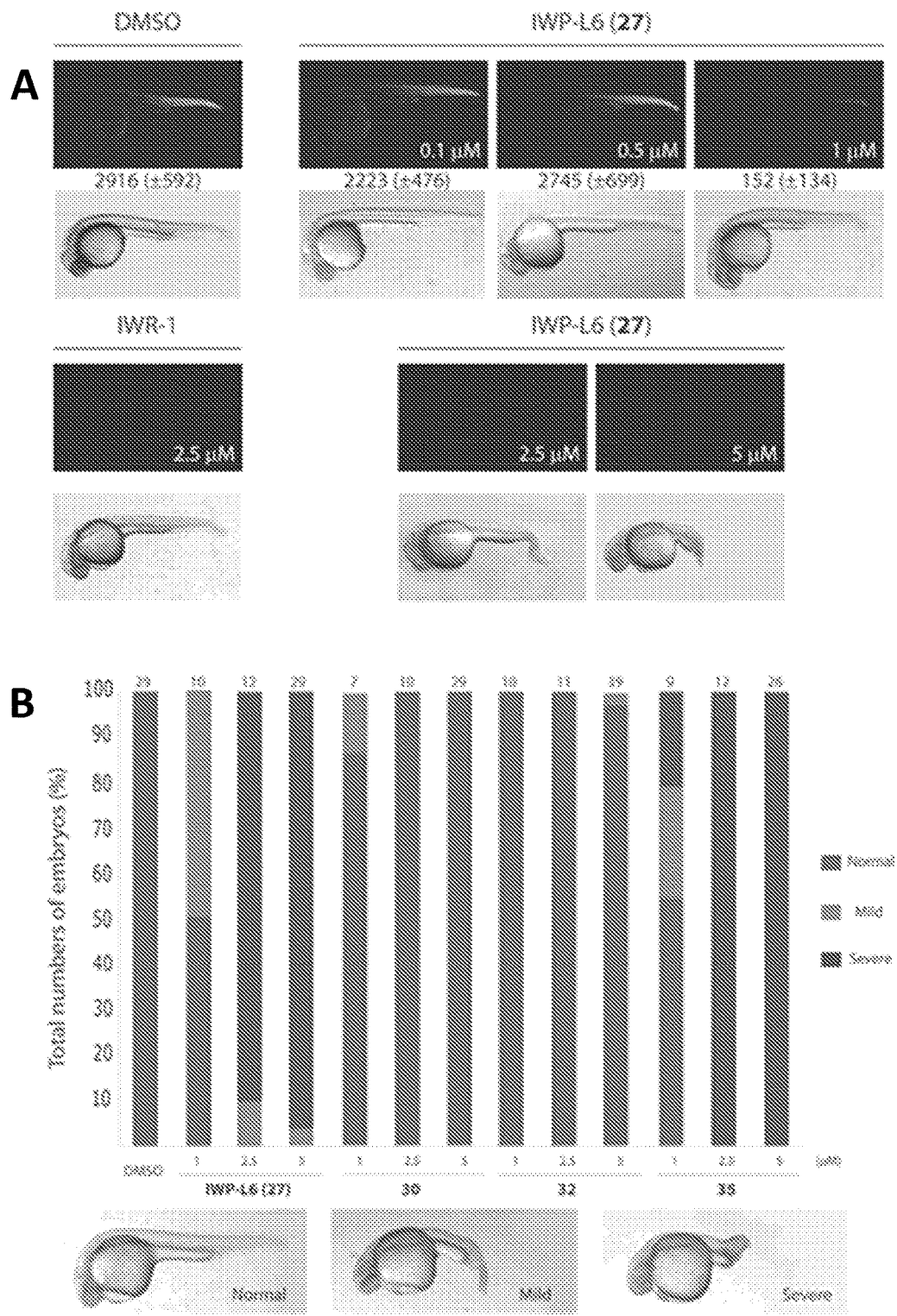
FIGS. 7A-B

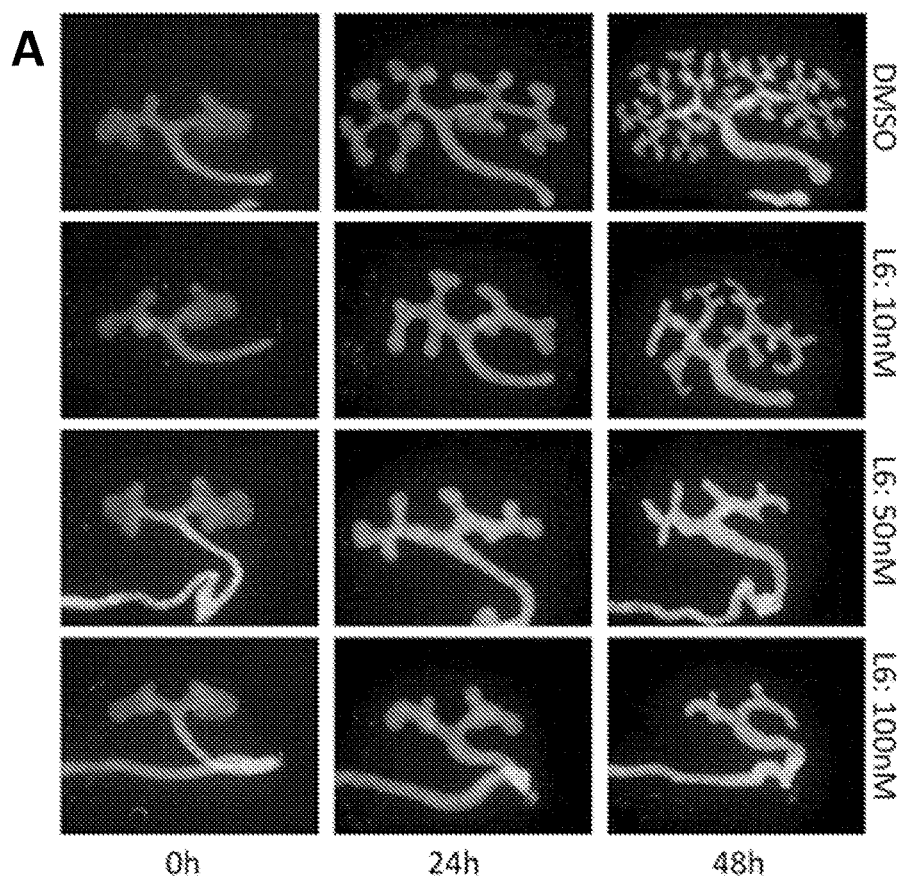
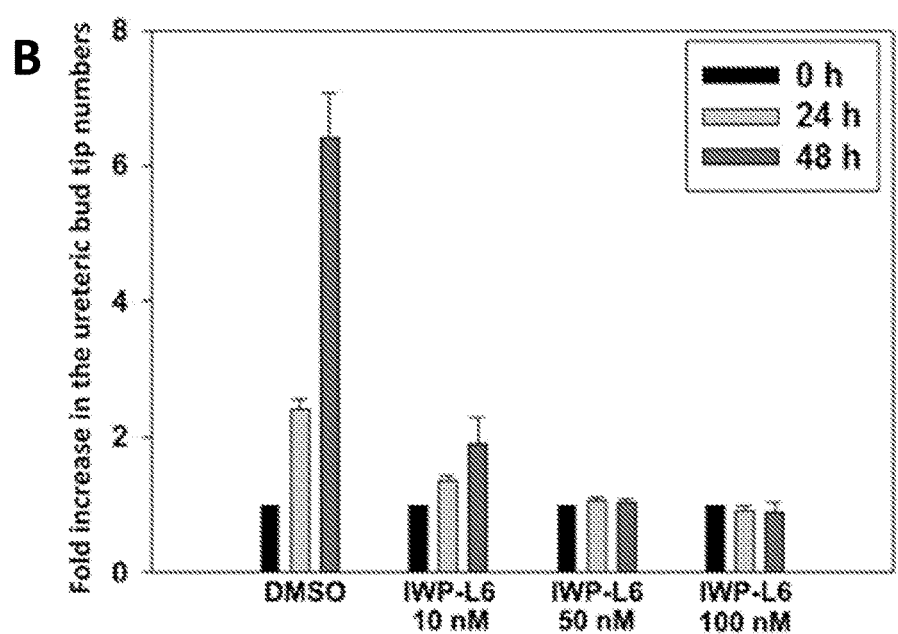
FIGS. 8A-B

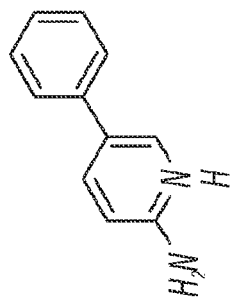
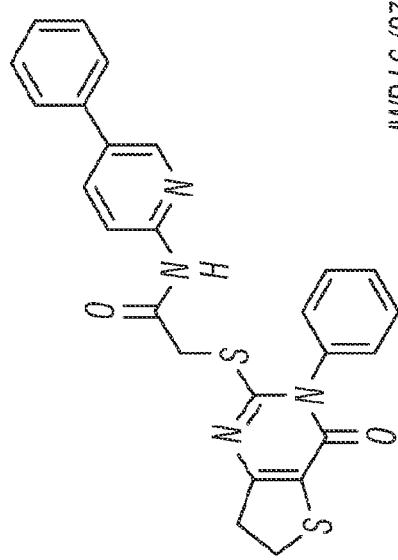
FIG. 9E

HIGHLY POTENT INHIBITORS OF PORCUPINE

This application is a national phase application under 35 U.S.C. §371 of International Application No. PCT/US2014/037980, filed May 14, 2014, which claims benefit of priority to U.S. Provisional Application Ser. No. 61/823,209, filed May 14, 2013, the entire contents of each of which are hereby incorporated by reference.

This invention was made with government support under Grant Number 5R21HD061303 awarded by the National Institutes of Health. The government has certain rights in the invention.

BACKGROUND OF THE INVENTION

1. Field of the Invention

The present invention generally relates to the fields of molecular biology and medicine. More particularly, it concerns the identification of compounds that inhibit Wnt-mediated signal transduction pathways, through interactions with the porcupine protein.

2. Description of Related Art

The evolutionary elaboration of gene families in complex multicellular animals provides diverse instructive cellular cues based on single signaling modalities and safeguards against genetic insults. During development, members of the Wnt family of signaling molecules—nineteen in all—contribute to almost all aspects of vertebrate development through induction of unique and shared cellular responses (Angers and Moon, 2009; van Amerongen and Nusse, 2009). In post-embryonic animals, their functions are essential to homeostatic tissue renewal and regeneration (Reya and Clevers, 2005). Previous work has lead to the development of inhibitors of the Wnt pathway and shown that the inhibitors' physiological target is Porcupine (Porcn), a membrane-bound O-acyltransferase (MBOAT) family protein (Chen et al., 2009; Yang et al., 2008). This acyltransferase catalyzes the palmitoylation of Wnt enabling its exit from the secretory pathway and subsequent activation of cellular responses. Compromised Porcn activity commonly results in developmental disorders including focal dermal hypoplasia (Goltz syndrome) whereas hyperactivity of Porcn is associated with cancerous cell growth (Che, et al., 2008) The inhibition of Porcn is envisioned to be an effective strategy for broadly suppressing Wnt signaling and thus hold potential in regenerative medicine and anti-cancer applications. Although genetically based targeting of Wnt signaling components suggests that chemical inhibitors of Wnt signaling may give rise to toxic effects, Porcn inhibitors have proven to be remarkably non-toxic in rodents (Proffitt et al., 2013).

Accordingly, identification of methods and compounds that modulate the Wnt-dependent cellular responses may offer an avenue for therapeutic treatment of diseases associated with aberrant activity of these pathways.

SUMMARY OF THE INVENTION

The present invention generally provides compounds and their use as Wnt protein signalling inhibitors. Also provided are methods of synthesis of these compounds and pharmaceutical compositions thereof.

The present invention generally provides a compound of the formula:

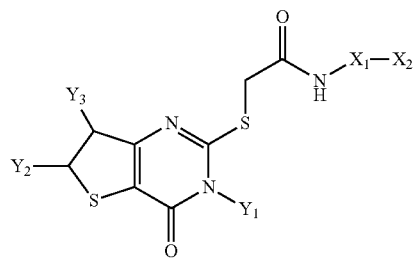

wherein: $X_1$ is arenediyl$_{(C\leq 8)}$, heteroarenediyl$_{(C\leq 8)}$ or a substituted version of any of these groups; $X_2$ is aryl$_{(C\leq 8)}$, heteroaryl$_{(C\leq 8)}$, or a substituted version of any of these groups; $Y_1$ is alkyl$_{(C\leq 8)}$, aryl$_{(C\leq 8)}$, or a substituted version of any of these groups; $Y_2$ or $Y_3$ are each independently hydrogen, halo, hydroxy, alkoxy$_{(C\leq 8)}$, alkyl$_{(C\leq 8)}$, or a substituted version of any of these groups; or a pharmaceutically acceptable salt or tautomer thereof.

In some embodiments, $Y_1$ is aryl$_{(C\leq 8)}$. In some embodiments, $Y_1$ is phenyl. In some embodiments, $Y_2$ and $Y_3$ are hydrogen.

In some embodiments, $X_1$ is of the structure:

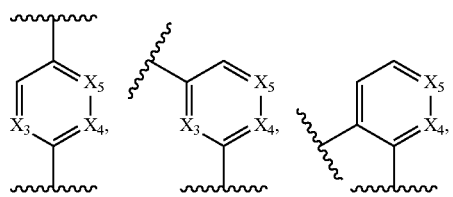

wherein: $X_3$, $X_4$, or $X_5$ are each independently CH or N; or a substituted version of any of these groups. In some embodiments, $X_1$ is of the structure:

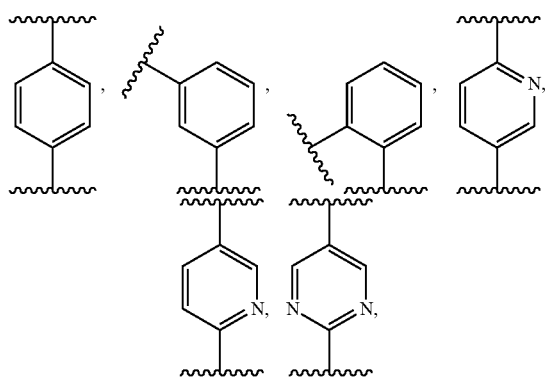

or a substituted version of any of these groups. In some embodiments, $X_1$ is of the structure:

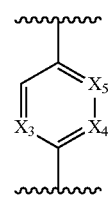

wherein: $X_3$, $X_4$, or $X_5$ are each independently CH or N; or a substituted version of this group. In some embodiments, $X_1$ is of the structure:

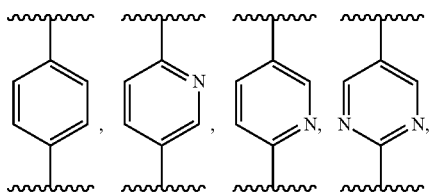

or a substituted version of any of these groups. In some embodiments, $X_1$ is not substituted.

In some embodiments, $X_2$ is aryl$_{(C≤8)}$ or a substituted aryl$_{(C≤8)}$. In some embodiments, $X_2$ is heteroaryl$_{(C≤8)}$ or a substituted heteroaryl$_{(C≤8)}$. In some embodiments, $X_2$ is phenyl or a substituted version of this group. In some embodiments, $X_2$ is phenyl. In some embodiments, $X_2$ is pyridinyl, pyrimidinyl, furanyl, thienyl or a substituted version of any of these groups. In some embodiments, $X_2$ is 2-pyridinyl, 3-pyridinyl, 4-pyridinyl or a substituted version of any of these groups. In some embodiments, $X_2$ is 3-pyridinyl. In other embodiments, $X_2$ is 5-pyrimidinyl or a substituted 5-pyrimidinyl. In other embodiments, $X_2$ is 2-furanyl, 3-furanyl, or a substituted version of any of these groups. In other embodiments, $X_2$ is 2-thienyl, 3-thienyl, or a substituted version of any of these groups. In other embodiments, $X_2$ is 2-thienyl. In some embodiments, $X_2$ is not substituted. In some embodiments, the compound is:

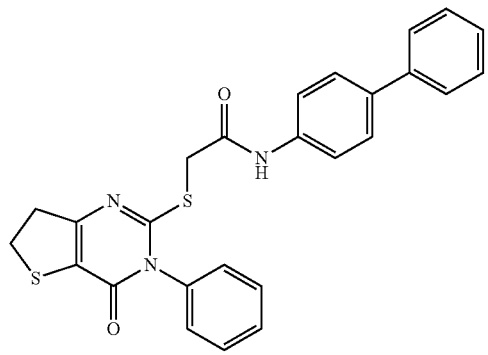

,

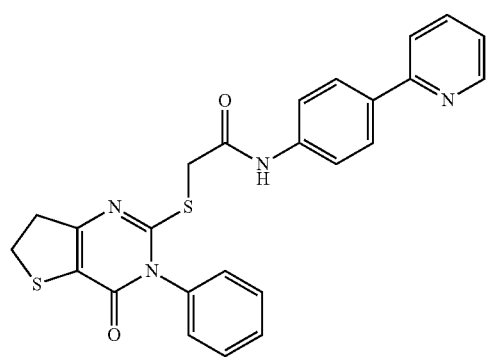

,

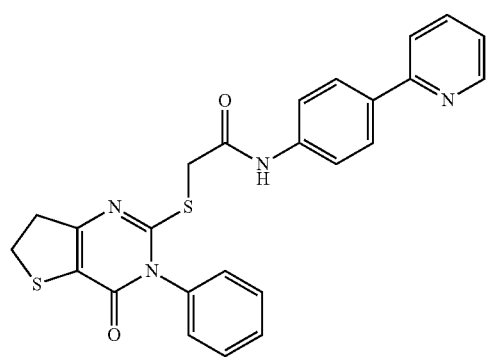

,

-continued

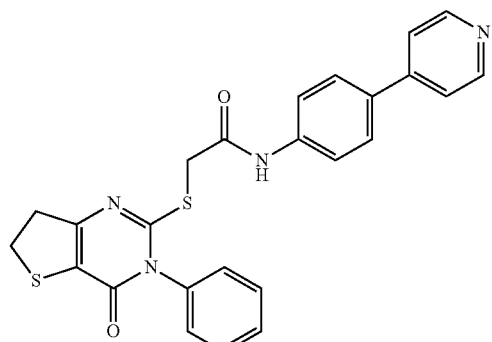

,

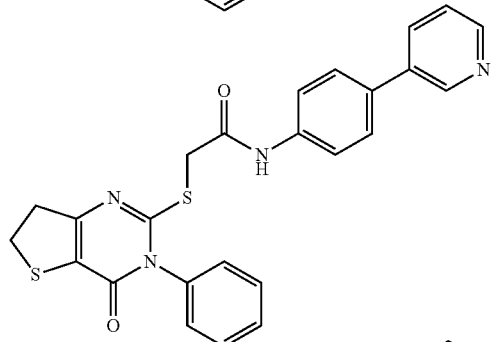

,

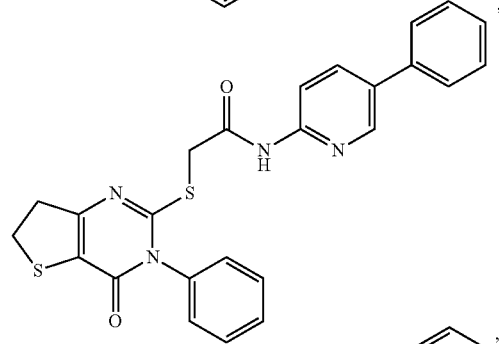

,

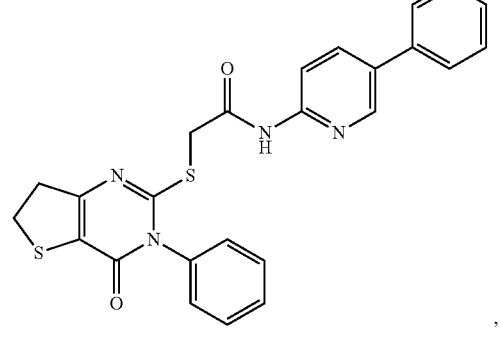

,

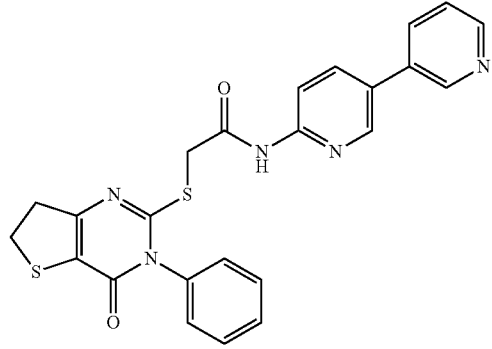

,

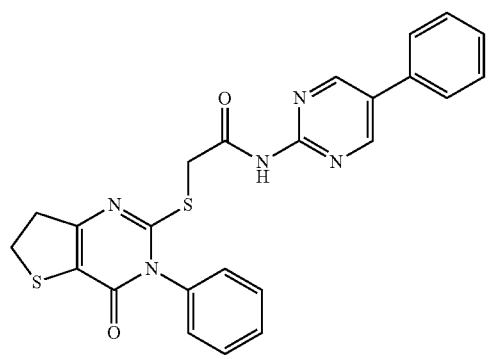
,
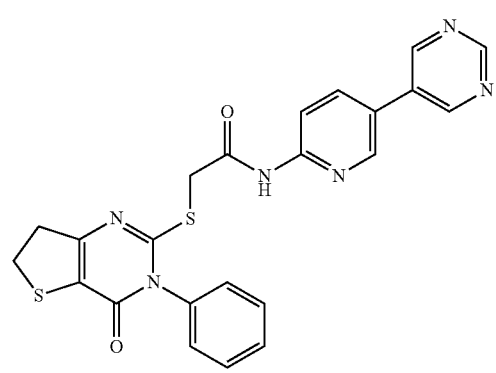
,
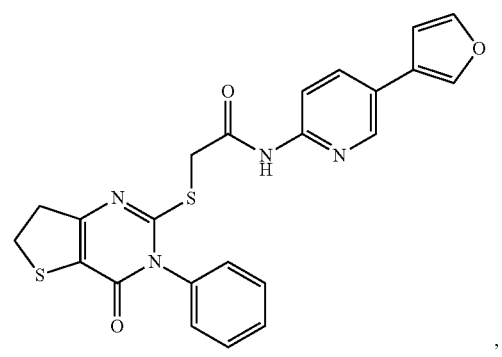
,
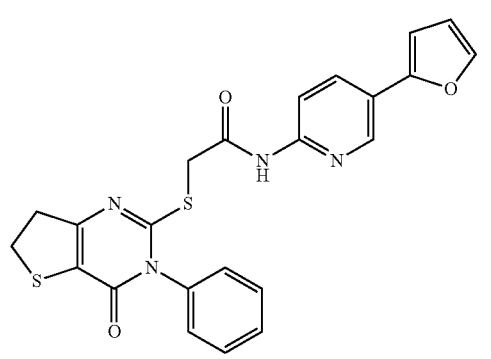
,
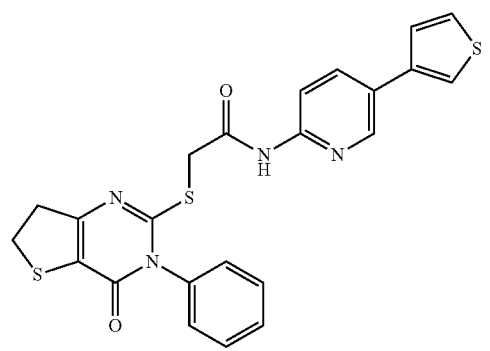
,
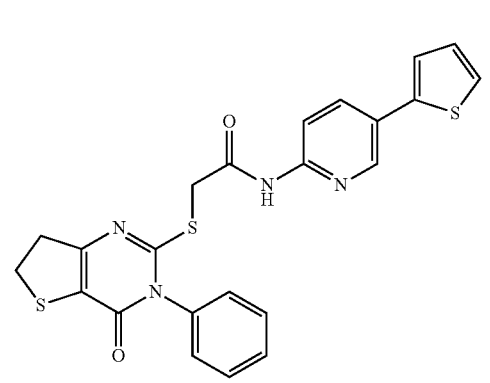
,
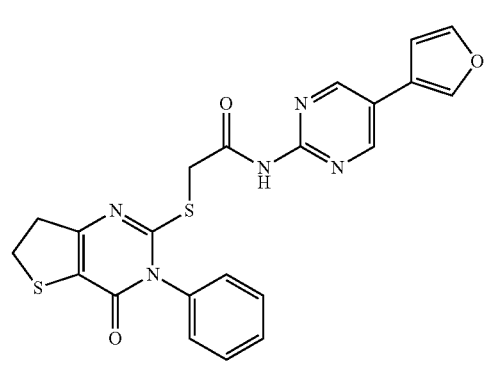
,
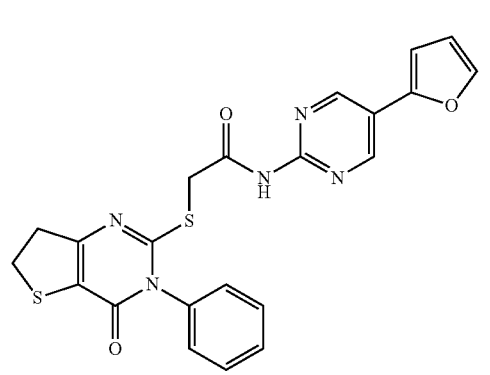
,

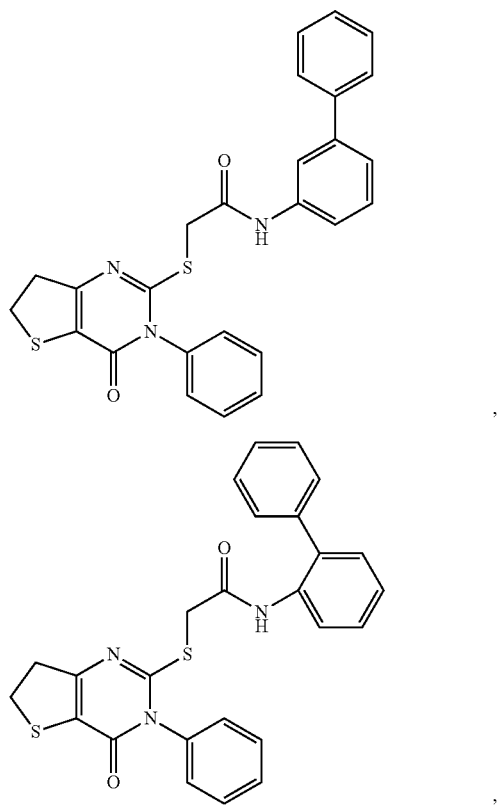

,

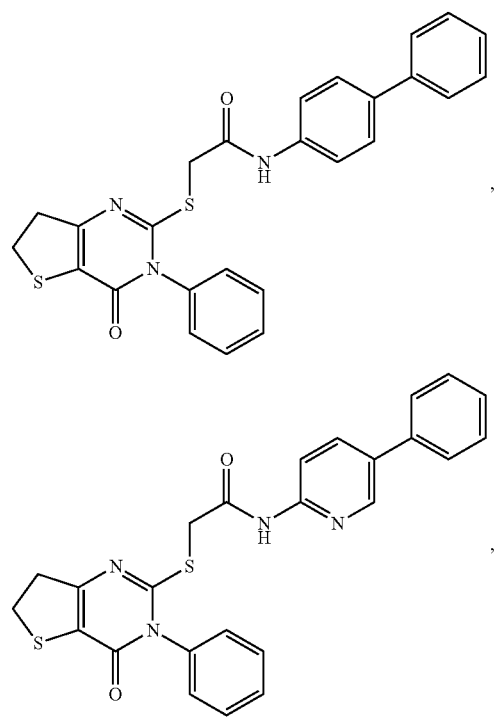

, or a pharmaceutically acceptable salt or tautomer thereof.

In some embodiments, the compounds are further defined as:

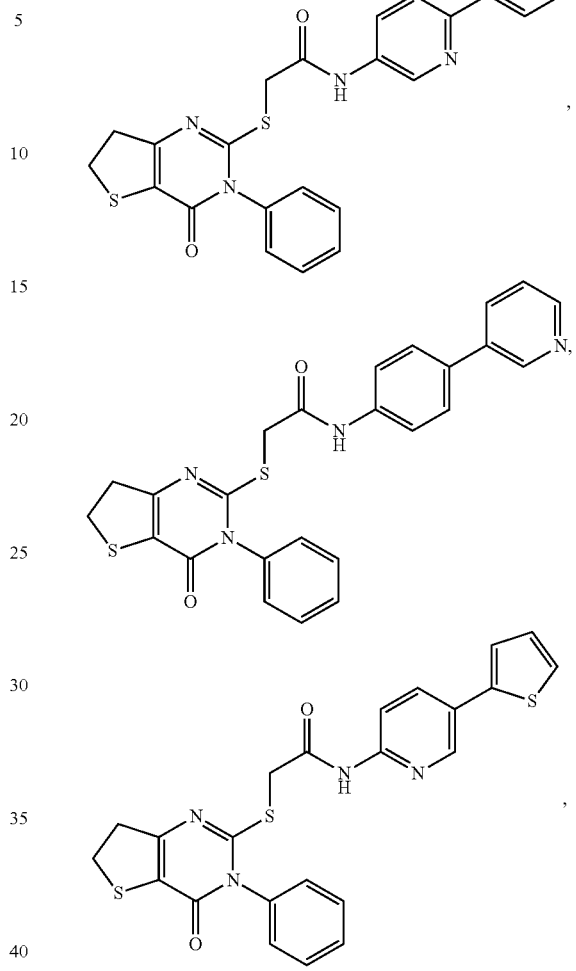

or a pharmaceutically acceptable salt or tautomer thereof.

In other embodiments, the present disclosure describes a method of inhibiting a Wnt protein signaling in a cell comprising administering to the cell an effective amount of a compound described in this disclosure. In some embodiments, the administration is performed in vitro. In other embodiments, the administration is performed in vivo. In some embodiments, the method of inhibiting Wnt protein signaling is further defined as a method of inhibiting Wnt response. In other embodiments, the method of inhibiting Wnt protein signaling is further defined as a method of inhibiting Wnt protein production. In other embodiments, the method further comprises administering to said cell an inhibitor of Porcn.

In other embodiments, the present disclosure describes a method of treating cancer in a subject comprising administering to the subject an effective amount of a compound described in this disclosure. In some embodiments, the method further comprises administering to said subject an inhibitor of Porcn. In some embodiments, the compound is comprised with a pharmaceutically acceptable carrier, diluent, and/or excipient in a pharmaceutical composition. In some embodiments, the cancer is colorectal cancer, breast cancer, liver cancer, lung cancer, or prostate cancer. In other embodiments, the method further comprises administration of a chemotherapeutic, radiation therapy, immunotherapy, hormone therapy, toxin therapy, or gene therapy. In some embodiments, the method of administration is selected from the group consisting of intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation, via injection, via infusion, via continuous infusion, via localized perfusion bathing target cells directly, via a catheter, via a lavage, in cremes, in lipid compositions, or any combination thereof.

In other embodiments, the present disclosure describes a method of treating or preventing osteopetrosis in a patient comprising administering to the patient an effective amount of a compound described in this disclosure. In some embodiments, the method further comprises administering to said cell an inhibitor of Porcn. In other embodiments, the method further comprises administration of a second osteopetrosis-treating agent or a second osteopetrosis-preventing agent. In some embodiments, the method of administration is selected from the group consisting of intravenously, intradermally, intraarterially, intraperitoneally, intralesionally, intracranially, intraarticularly, intranasally, topically, intramuscularly, subcutaneously, intraumbilically, orally, locally, via inhalation, via injection, via infusion, via continuous infusion, via localized perfusion bathing target cells directly, via a catheter, in cremes, in lipid compositions, or any combination thereof. In some embodiments, treating comprises slowing the onset of osteoporosis. In other embodiments, treating comprises slowing the progression of osteoporosis.

In other embodiments, the present disclosure describes a method of treating a degenerative disease in a patient comprising administering to the patient an effective amount of a compound described in this disclosure. In some embodiments, the method further comprises administering to said cell an inhibitor of Porcn. In other embodiments, the method further comprises administration of a second degenerative disease-treating agent or a second a degenerative disease-preventing agent. In some embodiments, the method of administration is selected from the group consisting of intravenously, intradermally, intraarterially, intraperitoneally, intralesionally, intracranially, intraarticularly, intranasally, topically, intramuscularly, subcutaneously, intraumbilically, orally, locally, via inhalation, via injection, via infusion, via continuous infusion, via localized perfusion bathing target cells directly, via a catheter, in cremes, in lipid compositions, or any combination thereof. In some embodiments, the degenerative disease is age-related impairment of tissue repair. In other embodiments, the degenerative disease is type II diabetes.

In other embodiments, the present disclosure describes a pharmaceutical composition comprising a pharmaceutically acceptable carrier, diluent, and/or excipient and a compound described in this disclosure.

In another aspect, the present disclosure describes a method for the preparation of a compound of formula III comprising reacting an amine of the formula, $NH_2-X_1-X_2$ with a compound of the formula:

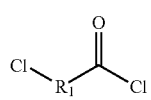

(II)

to form a compound of the formula:

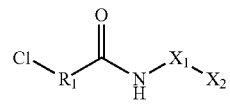

(III)

wherein: $X_1$ is arenediyl$_{(C \leq 8)}$, heteroarenediyl$_{(C \leq 8)}$ or a substituted version of any of these groups; $X_2$ is aryl$_{(C \leq 8)}$, heteroaryl$_{(C \leq 8)}$, or a substituted version of any of these groups; $R_1$ is alkanediyl$_{(C \leq 8)}$. In some embodiments, the method further comprises combining formula II and formula III in an organic solvent or a mixture of solvents. In some embodiments, the solvents are selected from methanol, ethanol, acetone, acetonitrile, chloroform, dichloromethane, dimethylformamide; dimethylsulfoxide, dioxane, benzene, tetrahydrofuran, ethyl acetate, hexane, or diethyl ether. In other embodiments, the solvent is a mixture of benzene and tetrahydrofuran. In other embodiments, the solvent is a 9:1 benzene:tetrahydrofuran mixture. In some embodiments, the method is further comprises heating the mixture of formula III and formula IV to 40-60° C. In some embodiments, the mixture is heated to 50° C. In some embodiments, the method further comprises allowing formula II and formula III to mix for 8-24 hours. In some embodiments, the formulas are allowed to mix for 12 hours. In some embodiments, the method further comprises reacting a compound of formula (III) with a compound of the formula:

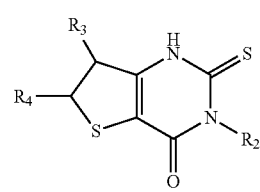

(IV)

to form a compound of the formula:

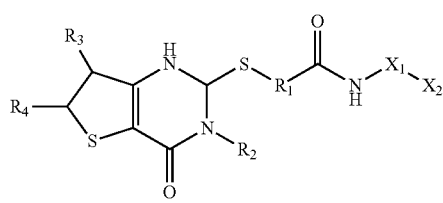

(V)

wherein: $X_1$ is arenediyl$_{(C \leq 8)}$, heteroarenediyl$_{(C \leq 8)}$ or a substituted version of any of these groups; $X_2$ is aryl$_{(C \leq 8)}$, heteroaryl$_{(C \leq 8)}$, or a substituted version of any of these groups; $R_1$ is alkanediyl$_{(C \leq 8)}$; $R_2$ is alkyl$_{(C \leq 8)}$, acyl$_{(C \leq 8)}$, aryl$_{(C \leq 8)}$, or a substituted version of any of these groups; $R_3$ and $R_4$ are alkyl$_{(C \leq 8)}$, alkenyl$_{(C \leq 8)}$, aryl$_{(C \leq 8)}$, aralkyl$_{(C \leq 8)}$, or a substituted version of any of the groups. In some embodiments, the method further comprises combining formula III and formula IV in an organic solvent or a mixture of solvents. In some embodiments, the solvents are selected from methanol, ethanol, acetone, acetonitrile, chloroform, dichloromethane, dimethylformamide; dimethylsulfoxide, dioxane, benzene, tetrahydrofuran, ethyl acetate, hexane, or diethyl ether. In some embodiments, the solvent is a dimethylformamide. In some embodiments, the method further comprises heating the mixture of formula III and formula IV to 70-90° C. In some embodiments, the reaction is heated to 80° C. In some embodiments, the method further comprises allowing formula III and formula IV to mix for 1-4 hours. In some embodiments, the formulas are allowed to mix for 2 hours. In some embodiments,

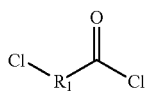

is 2-chloroacetyl chloride. In some embodiments,

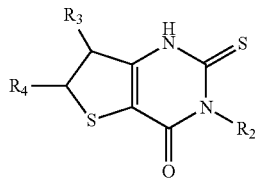

is 3-phenyl-6,7-dihydrothieno[3,2-d]pyrimidine-2-thione-4-one.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 7A-B—(FIG. 7A) IWP-L6 (FIG. 3 Compound 27) inhibits posterior axis formation. Zebrafish embryos harboring a mCherry-based reporter of Wnt/β-catenin signaling (Moro, et al., 2012) were treated with increasing concentrations of IWP-L6 (FIG. 3 Compound 27) in the aquarium water. Fluorescence intensity of animals was quantified as before (Dodge et al., 2012). (FIG. 7B) Activity of the IWP compounds IWP-L6 (Compound 27), 30, 32, and 35 was measured using the posterior axis formation assay.

FIGS. 8A-B—(FIG. 8A) IWP-L6 (Compound 27) inhibits Wnt mediated branching morphogenesis in cultured embryonic kidneys. Hoxb7Cre; RosaTomato kidneys were dissected from E11.5 embryos and cultured at the air/media interface (Dodge, et al., 2012; Kamer, et al., 2010) Media was replaced every 24 hours. Images were captured every 24 hours using a Zeiss Lumar V12 fluorescent stereoscope. Magnitude: 80× at 0 hours and 24 hours; 60× at 48 hours. (FIG. 8B) The fold increase in the number of ureteric bud tips between time=0 and 48 hours for each treatment was quantified. Statistics were performed using Student T-test.

FIGS. 9A-E—(FIG. 9A) Graph showing the rate of the metabolism of IWP-L6 in murine S9 fractions. (FIG. 9B) Graph showing the rate of cleavage of the amide of IWP-L6 in mouse plasma. (FIG. 9C) Graph showing the rate of cleavage of the amide of IWP-L6 in rat plasma. (FIG. 9D) Graph showing the rate of cleavage of the amide in IWP-L6 in human plasma. (FIG. 9E) The structure of IWP-L6 and its metabolite.

(FIG. 11B) $^{13}$C NMR spectra for IWP-L6. (FIG. 11C) $^{13}$C NMR spectra for IWP-L6, enlarged.

DESCRIPTION OF ILLUSTRATIVE EMBODIMENTS

Figure 1:
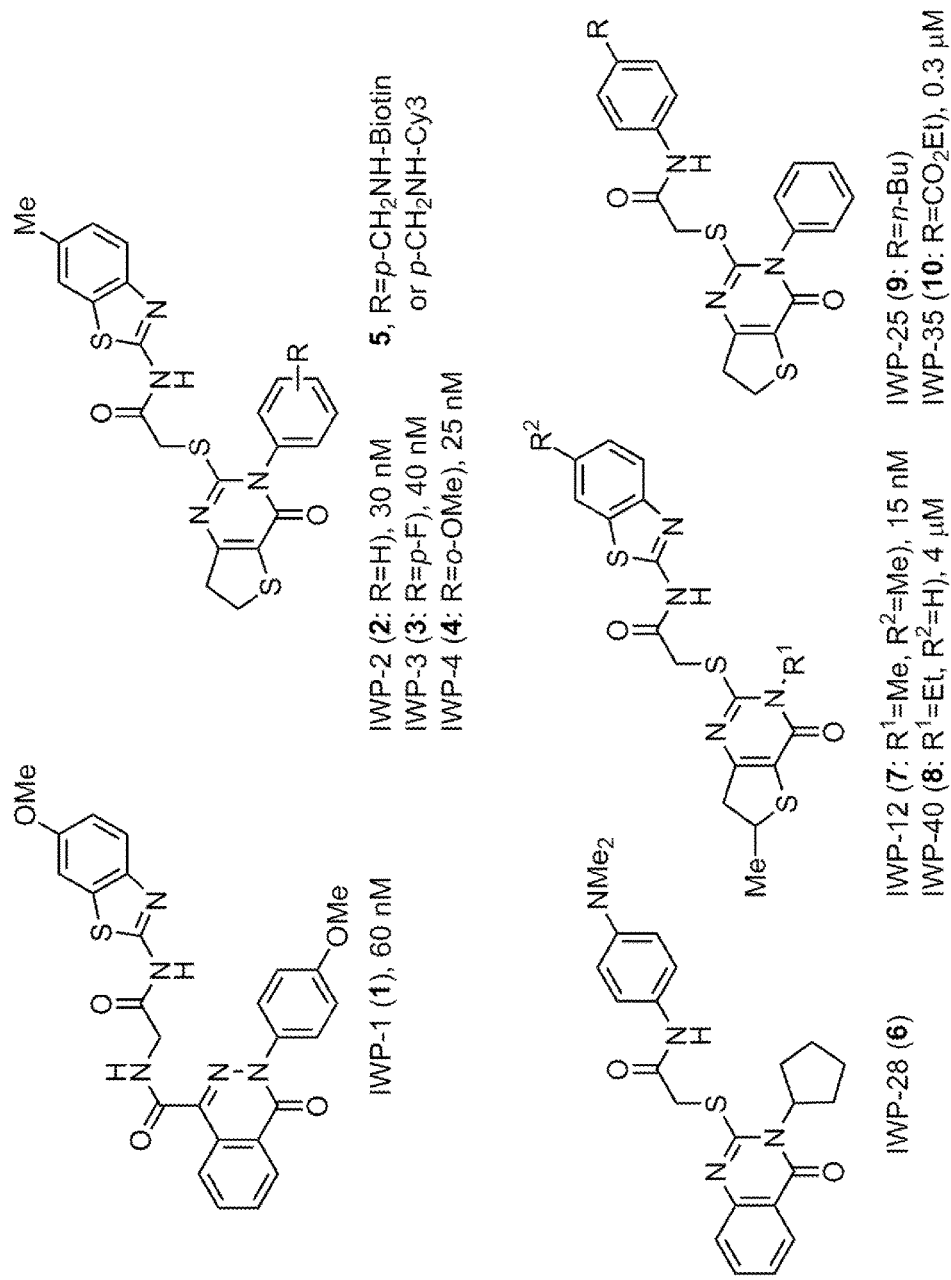
FIG. 1—The structures and activities of previous inhibitors of Wnt proteins (IWPs) identified from a high-throughput screen in cells exhibiting cell-autonomous Wnt signaling.

Chemically-based strategies are ideally suited for studying the molecular basis of complex biological phenomena given the potential of small molecules to overcome some of these limitations. Previously, the inventors described two classes of small molecules that disengage Wnt-mediated responses (Chen et al., 2009). In these cases, the Inhibitors of Wnt Response (IWR) compounds target the Tankyrase (Tnks) enzymes that regulate Axin protein turnover, scaffolding molecules in the β-catenin destruction complex (Chen et al., 2009; Huang and He, 2008). In the absence of Tnks activity, Axin proteins accumulate and accelerate the rate of β-catenin destruction. On the other hand, the Inhibitor of Wnt Production (IWP) compounds disrupt Wnt signaling by preventing Porcndependent lipidation of Wnt proteins. Porcn is the founding member of the membrane bound O-acyltransferase (MBOAT) family that consists of 16 family members (Yang et al., 2008). Likely due to their limited bioavailability, the IWP compounds, unlike the IWR compounds, exhibited little in vivo activity (Chen et al., 2009). Instead, IWP compounds have been extensively used in a variety of in vitro settings for tissue engineering and stem cell biology (Ren et al., 2011; Sato et al., 2011; ten Berge et al., 2011).

In order to expand the utility of Porcn inhibitors to include in vivo studies, the current disclosure relates to additional Porcn compounds developed through chemical modification of previous Wnt pathway inhibitors which appear to directly engage Porcn at its putative active site thus revealing Porcn to be a highly druggable enzyme. Previous work illustrates that this protein has a role in Wnt protein lipidation in promoting diverse Wnt-mediated responses in development and tissue regeneration, and establish a chemical toolkit for interrogating Wnt signaling mechanisms in these contexts. Small molecules that target Wnt-dependent signal transduction pathways reveal chemically-sensitive regulatory mechanisms within these signal transduction pathway that may be exploited by pharmacological means for medical use, such as regenerative and anti-cancer therapy.

I. The Wnt Signal Transduction Pathways

The Wnt gene family encodes secreted ligand proteins that serve an important role in differentiation and development. This family comprises at least 19 vertebrate and invertebrate genes including the *Drosophila* segment polarity gene wingless and one of its vertebrate homologues, integrated from which the Wnt name derives. As noted above, the Wnt proteins appear to facilitate a number of developmental and homeostatic processes.

The Wnt signaling pathways comprises a number of proteins involved in the transduction of cellular responses to secreted Wnt/wingless signalling proteins. Wnt proteins that control "non-canonical" pathways, such as the Wnt/calcium and planar cell polarity pathways, induce cellular responses that are not dependent upon β-catenin. In the Wnt/β-catenin pathway, the Frizzled receptor then activates Disheveled protein, which blocks the inhibiting action of Zeste-white-3 kinase (or GSK3β in vertebrates, Glycogen Synthase Kinase-3β) upon the Armadillo protein (a β-catenin protein). The β-catenin protein transduces the Wnt signal from the cytoplasm to the nucleus. In the absence of Wnt signalling, β-catenin is constitutively degraded by the proteasome and can be found in a multimeric complex with conductin (or axin), APC (Adenomatous Polyposis Coli) and GSK3β. APC mediates the binding of β-catenin to conductin and serves to activate the conductin protein. Conductin acts as a scaffold to assemble the components of the degradation pathway of β-catenin. GSK3β, a serine/threonine kinase, phosphorylates β-catenin, thus stimulating its degradation by the proteasome.

Upon Wnt signaling, GSK3β kinase is inactivated, leading to stabilization of the β-catenin protein. β-Catenin is then released from the multimeric complex and translocates into the nucleus. Once in the nucleus, β-catenin interacts with the LEF/TCF (Lymphoid Enhancer Factor/T-Cell Factor) family of HMG (High Mobility Group) box transcription factors. The LEF/TCF factors are stimulated through interaction with β-catenin to become potent transactivators of a number of genes including c-myc and cyclin D1.

II. Therapeutic Implications Of Wnt-Controlled Signal Transduction Pathways

As noted above, evidence suggests that targeting the Wnt-mediated signal transduction pathways would be therapeutically useful in a broad range of diseases (Barker and Clevers, 2006; Veeman et al, 2003). Aged mice or mice that exhibit premature stem cell senescence that are treated with extracellular protein inhibitors of Wnt pathways exhibit improved regenerative capacity in various tissues (Brack et al., 2007; Liu et al., 2007). Mutations leading to constitutive activation of the Wnt pathway are critical events in a variety of human cancers including colon cancer, melanoma, hepatocellular carcinoma and others. The end result of constitutive activation of the Wnt/β-catenin pathway is a dramatic increase in the level of β-catenin protein in the cytoplasm. Inappropriate stabilization of β-catenin, leading to increased levels of the protein, can be caused by mutations in a variety of proteins in the Wnt signalling pathway. Blockade of the Wnt/β-catenin pathway in a variety of cancers using either genetic or chemical approaches been shown to abrogate aberrant cell growth (Barker and Clevers, 2006). Furthermore, inhibition of this pathway may directly influence the cells that sustain cancer cell growth and enable metastasis, and that are thought to be resistant to traditional chemotherapeutic agents (Ailles and Weissman, 2007).

The pervasive influence of the Wnt proteins in tissue homeostasis and tumorigenesis suggests areas such as regenerative medicine and anti-cancer therapy may benefit from therapies that target this pathway. Achieving transient repression of pathological Wnt response without incurring permanent damage to normal stem cell function is a key anticancer therapeutic goal. The inventors tested for the ability of zebrafish to resume regenerative processes following a chemically induced blockade of fin regrowth. Fish with resected caudal fins that were bred in water containing IWP-L6 for 7 d were able to regenerate tissue to nearly normal levels after chemical removal, which suggests that transient inhibition of Wnt/β-catenin response does not permanently alter the ability of stem cells to self-renew.

Aberrant Wnt-mediated pathway responses, sustained by genetic changes that result either in altered Wnt ligand activity or in altered functioning of pathway regulators, have been associated with a broad range of cancers. See Clevers, 2006 and Polakis, 2007, both of which are incorporated herein by reference. Notably, more than 90% of colorectal cancer (CRC) tumors harbor a loss-of-function mutation in APC, a suppressor of the Wnt/β-catenin pathway. See Sjoblom et al., 2006, which is incorporated herein by reference. Without being bound by theory, the ability of IWP compounds to interrupt palmitoylation of Wnt and thus prevent the protein's exit from the secretory pathway and ability to active other cellular processes suggests that they may block aberrant cell growth supported by hyperactivation of Wnt/β-catenin responses.

III. Wnt Protein Production Inhibitors

Accordingly, the present invention provides small molecules that inhibit the production of Wnt protein in the signaling pathway. These compounds are represented by the formulas:

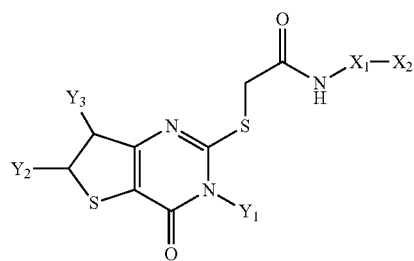

wherein: $X_1$ is arenediyl$_{(C \leq 8)}$, heteroarenediyl$_{(C \leq 8)}$ or a substituted version of any of these groups; $X_2$ is aryl$_{(C \leq 8)}$, heteroaryl$_{(C \leq 8)}$, or a substituted version of any of these groups; $Y_1$ is alkyl$_{(C \leq 8)}$, aryl$_{(C \leq 8)}$, or a substituted version of any of these groups; $Y_2$ or $Y_3$ are each independently hydrogen, halo, hydroxy, alkoxy$_{(C \leq 8)}$, alkyl$_{(C \leq 8)}$, or a substituted version of any of these groups; or a pharmaceutically acceptable salt or tautomer thereof. In some embodiments, $Y_1$ is aryl$_{(C \leq 8)}$. In some embodiments, $Y_1$ is phenyl. In some embodiments, $Y_2$ and $Y_3$ are hydrogen. In some embodiments, $X_1$ is of the structure:

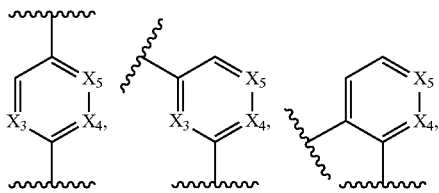

wherein: $X_3$, $X_4$, or $X_5$ are each independently CH or N; or a substituted version of any of these groups. In some embodiments, $X_1$ is of the structure:

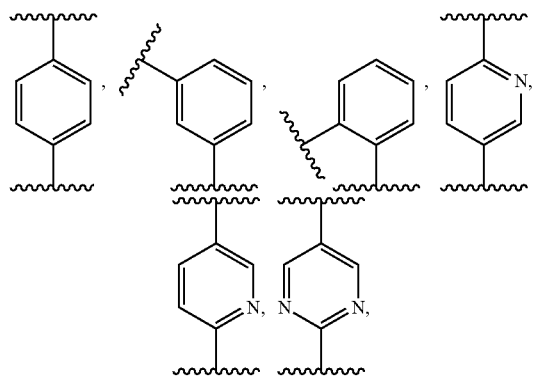

or a substituted version of any of these groups. In some embodiments, $X_1$ is of the structure:

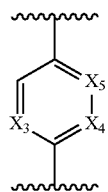

wherein: $X_3$, $X_4$, or $X_5$ are each independently CH or N; or a substituted version of this group.
In some embodiments, $X_1$ is of the structure:

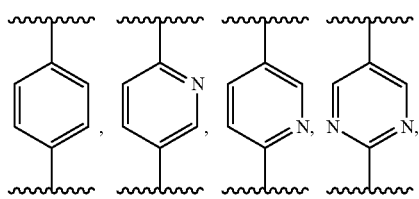

or a substituted version of any of these groups. In some embodiments, $X_1$ is not substituted.

In some embodiments, $X_2$ is aryl$_{(C \leq 8)}$ or a substituted aryl$_{(C \leq 8)}$. In some embodiments, $X_2$ is heteroaryl$_{(C \leq 8)}$ or a substituted heteroaryl$_{(C \leq 8)}$. In some embodiments, $X_2$ is phenyl or a substituted version of this group. In some embodiments, $X_2$ is phenyl. In some embodiments, $X_2$ is pyridinyl, pyrimidinyl, furanyl, thienyl or a substituted version of any of these groups. In some embodiments, $X_2$ is 2-pyridinyl, 3-pyridinyl, 4-pyridinyl or a substituted version of any of these groups. In some embodiments, $X_2$ is 3-pyridinyl. In some embodiments, $X_2$ is 5-pyrimidinyl or a substituted 5-pyrimidinyl. In some embodiments, $X_2$ is 2-furanyl, 3-furanyl, or a substituted version of any of these groups. In some embodiments, $X_2$ is 2-thienyl, 3-thienyl, or a substituted version of any of these groups. In some embodiments, $X_2$ is 2-thienyl. In some embodiments, $X_2$ is not substituted. In some embodiments, the inhibitor is a compound such as:

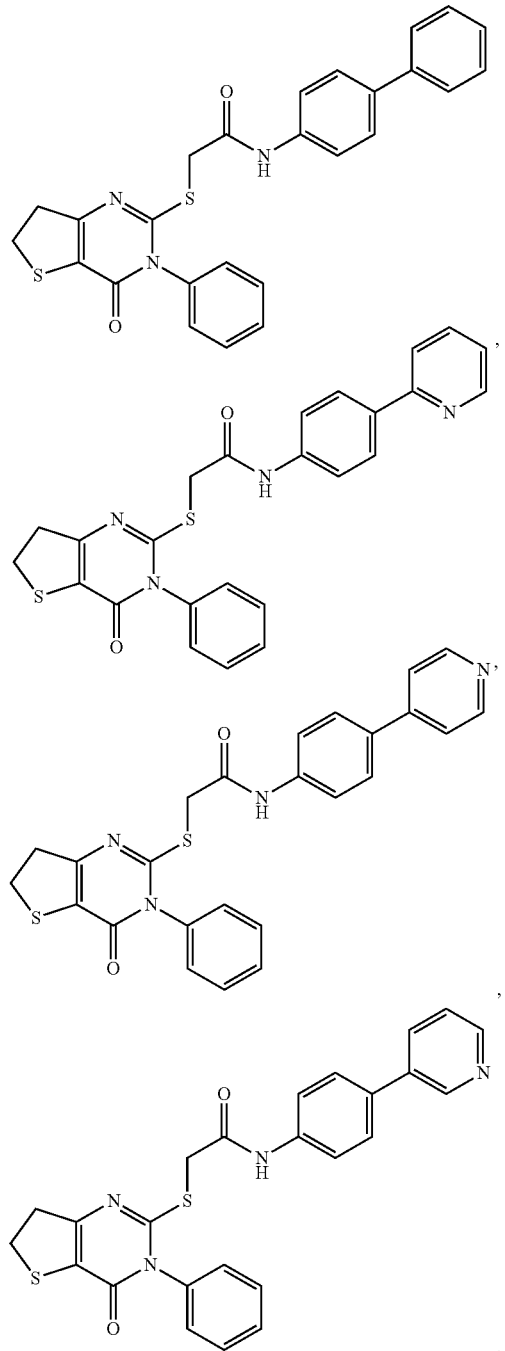

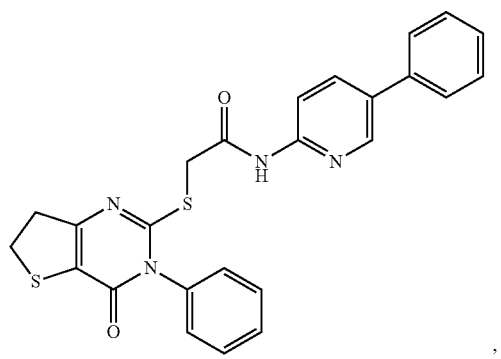
,
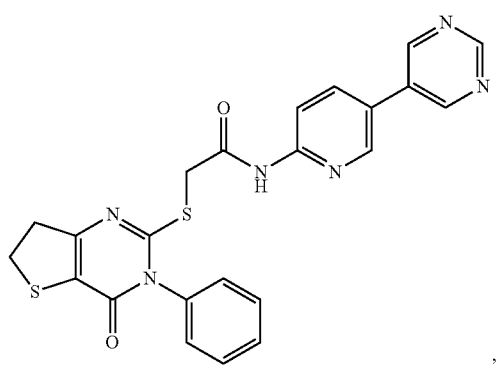
,
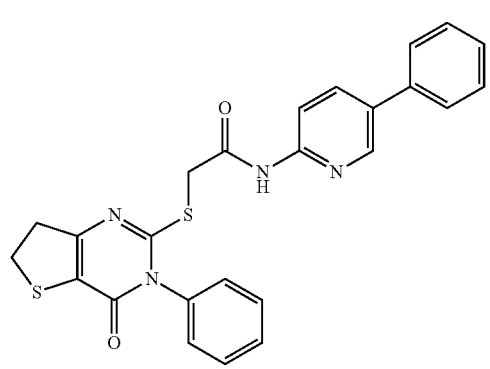
,
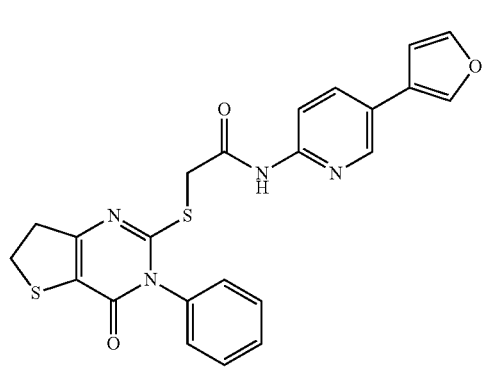
,
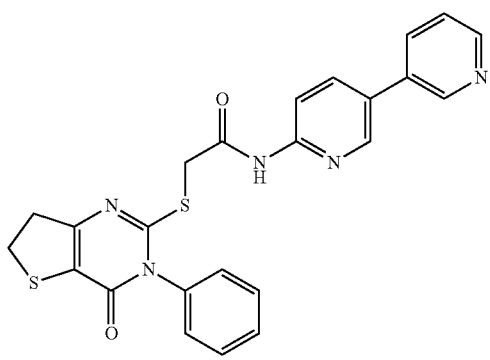
,
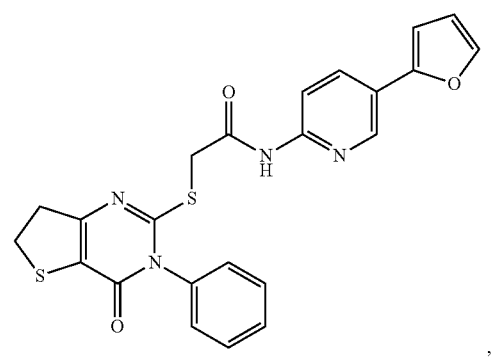
,
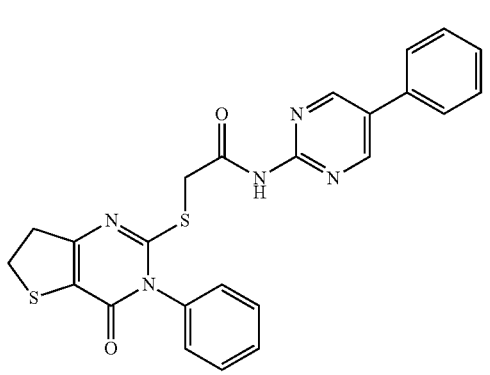
,
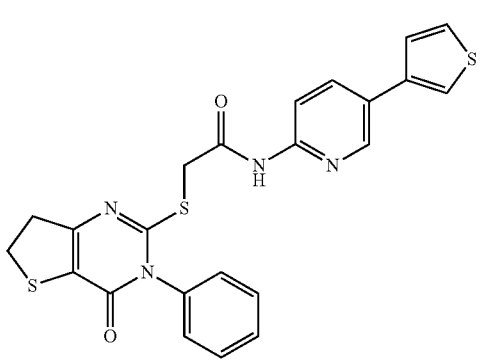
,

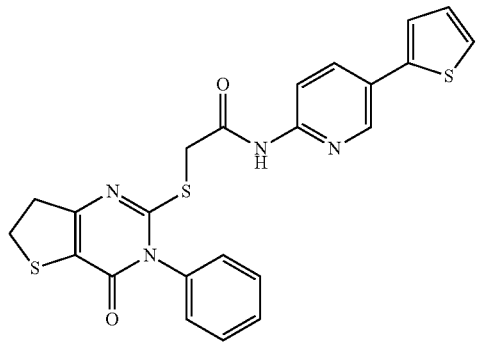
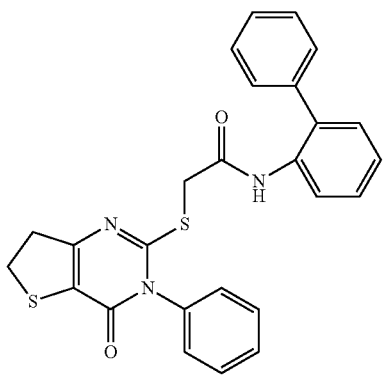
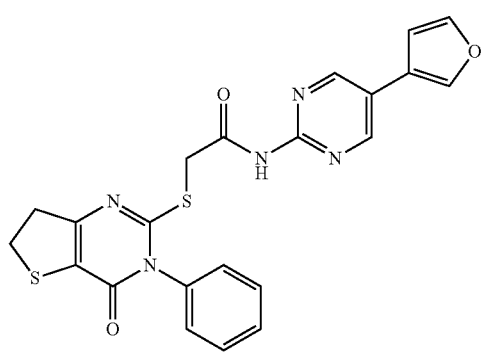
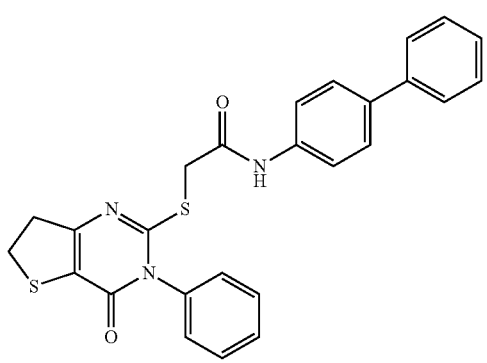
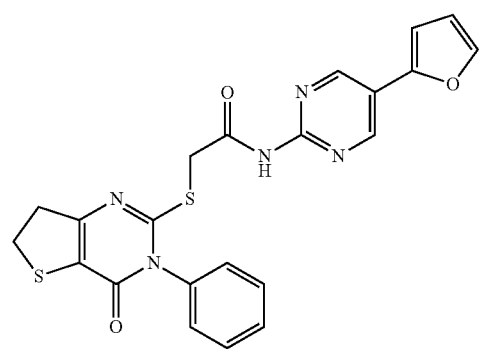
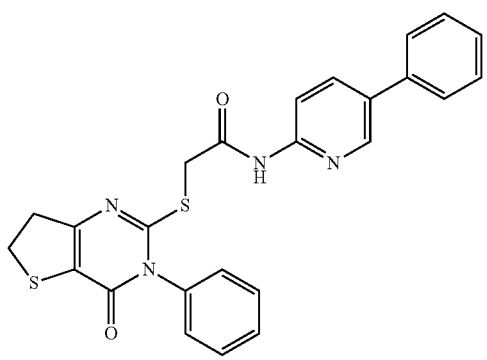
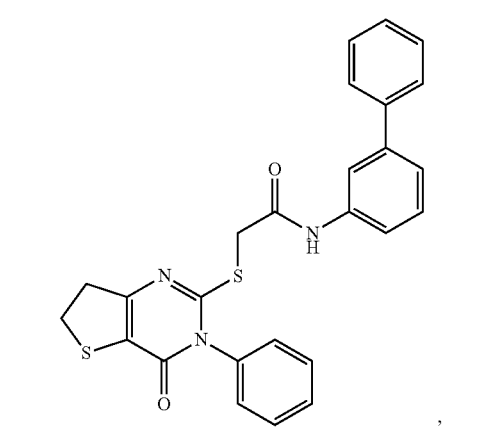
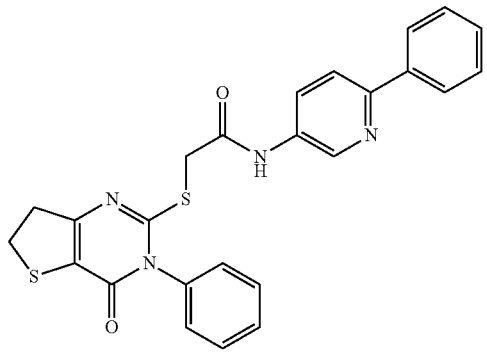
or a pharmaceutically acceptable salt or tautomer thereof. In some embodiments, the preferred inhibitor is a compound such as:

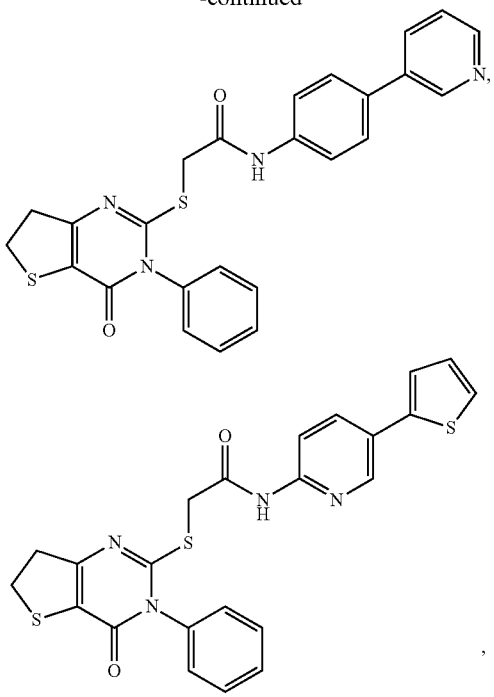

or a pharmaceutically acceptable salt or tautomer thereof

Such compounds can be synthesized using the methodology described in the synthetic scheme below:

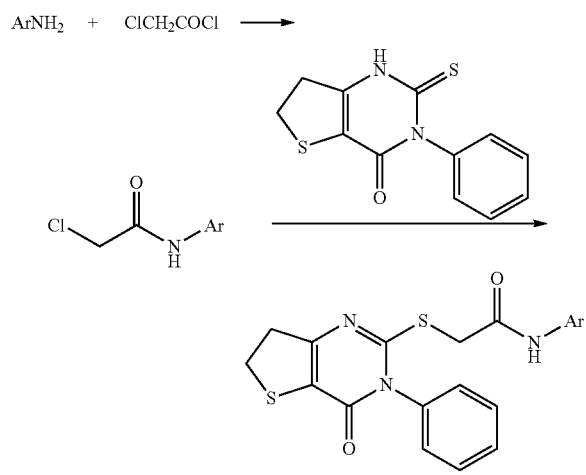

using standard methods known to one of skill in the art. The synthetic methodology described in this scheme is further elaborated in this disclosure.

All of these methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

IV. Definitions

As used herein, "Wnt protein signaling pathway" refers to the pathways by which binding of the Wnt protein to extracellular receptors is either translated into the nucleus and results in transcriptional activation of a variety of genes, or otherwise results in biochemical changes that influence cell behavior. The Wnt protein signaling pathways involve a variety of proteins including Frizzled, Disheveled, Axin, APC, GSK3β, β-catenin, LEF/TCF transcription factors, etc. Cells from many different species express homologs of the proteins involved in Wnt protein signaling pathways and accordingly have functionally equivalent Wnt protein signaling pathways.

As used herein, a "Wnt protein signaling inhibitor" is an organopharmaceutical (that is, a small organic molecule)

that inhibits Wnt protein signaling activity. Wnt protein signaling inhibitors typically have a molecular weight of about 1000 g/mol or less.

As used herein, a "Wnt protein production inhibitor" is an organopharmaceutical (that is, a small organic molecule) that inhibits Wnt protein production. Wnt protein production inhibitors typically have a molecular weight of about 1000 g/mol or less.

As used herein, "a method of inhibiting Wnt response" refers to methods of inhibiting known biochemical events associated with production of functional Wnt proteins or with cellular responses to Wnt proteins. As discussed herein, small organic molecules may inhibit Wnt response in accordance with this definition.

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "=====" represents a single bond or a double bond. Thus, for example, the structure

includes the structures

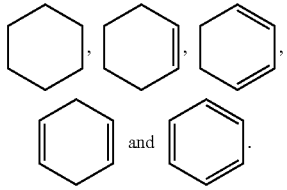

As will be understood by a person of skill in the art, no one such ring atom forms part of more than one double bond. The symbol "〰", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀━" means a single bond where the group attached to the thick end of the wedge is "out of the page." The symbol "▫▫▫▫▫" means a single bond where the group attached to the thick end of the wedge is "into the page". The symbol "〰" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

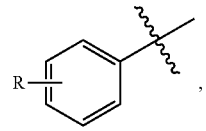

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

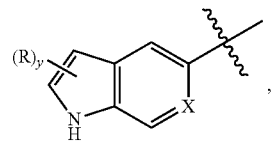

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

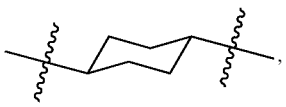 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halo-gen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CHF, —CF$_3$, and —CH$_2$CF$_3$ are non-limiting examples of fluoroalkyl groups. An "alkane" refers to the compound H—R, wherein R is alkyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

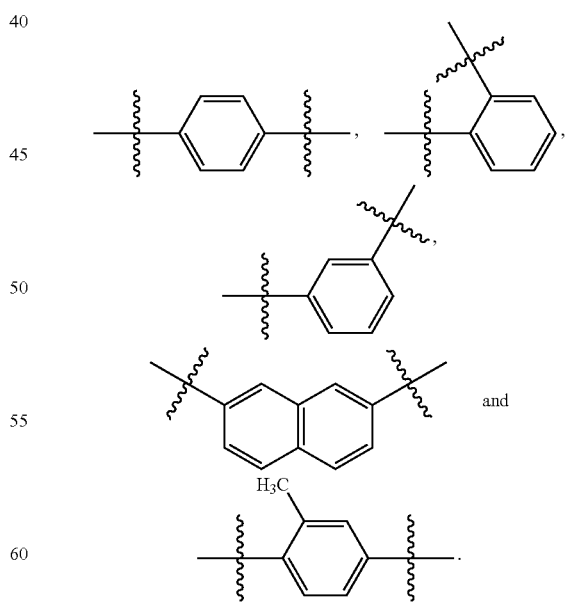

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)

CH₃, —N(CH₃)₂, —C(O)NH₂, —OC(O)CH₃, or —S(O)₂NH₂. An "arene" refers to the compound H—R, wherein R is aryl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

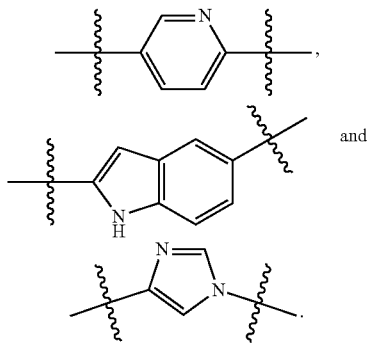

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC₅₀" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, $-[-CH_2CH_2-]_n-$, the repeat unit is $-CH_2CH_2-$. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art, such as methods described herein.

In certain aspects, "derivative" refers to a chemically-modified compound that still retains the desired effects of the compound prior to the chemical modification. A "Wnt protein production inhibitor derivative," therefore, refers to a chemically modified Wnt protein production inhibitor that still retains the desired effects of the parent Wnt protein production inhibitor prior to its chemical modification. Such effects may be enhanced (e.g., slightly more effective, twice as effective, etc.) or diminished (e.g., slightly less effective, 2-fold less effective, etc.) relative to the parent Wnt protein production inhibitor, but may still be considered a Wnt protein production inhibitor derivative. Such derivatives may have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide, and azo groups; sulfate, sulfonate, sulfono, sulfhydryl, sulfenyl, sulfonyl, sulfoxido, sulfonamide, phosphate, phosphono, phosphoryl groups, and halide substituents. Additional modifications can include an addition or a deletion of one or more atoms of the atomic framework, for example, substitution of an ethyl by a propyl, or substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present invention are also contemplated herein. The term "prodrug," as used herein, is understood as being a compound which, upon administration to a subject, such as a mammal, undergoes chemical conversion by metabolic or chemical processes to yield a compound any of the formulas herein, or a salt and/or solvate thereof. Solvates of the compounds of the present invention are preferably hydrates.

As used herein, "protecting group" refers to a moiety attached to a functional group to prevent an otherwise unwanted reaction of that functional group. The term "functional group" generally refers to how persons of skill in the art classify chemically reactive groups. Examples of functional groups include hydroxyl, amine, sulfhydryl, amide, carboxyl, carbonyl, etc. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999, incorporated herein by reference in its entirety. The Wnt protein signalling inhibitors described herein are also contemplated as protected by one or more protecting groups—that is, the inhibitors are contemplated in their "protected form."

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers.

Synthetic techniques that may be used to prepare certain compounds of the present invention are provided in the Examples section. Other synthetic techniques to prepare compounds of the present invention as well as derivatives are well-known to those of skill in the art. For example, March's Advanced Organic Chemistry: Reactions, Mechanisms, and Structure (2007) discuss a wide variety of synthetic transformations, reaction conditions, and possible pitfalls relating thereto. Methods discussed therein may be adapted to prepare compounds of the present invention from commercially available starting materials.

Solvent choices for preparing compounds of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In preferred embodiments, purification is performed via silica gel column chromatography or HPLC.

In view of the above definitions, other chemical terms used throughout this application can be easily understood by those of skill in the art. Terms may be used alone or in any combination thereof.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. Pharmaceutical Formulations And Routes For Administration

Pharmaceutical compositions of the present invention comprise an effective amount of one or more candidate substances (e.g., a Wnt protein production inhibitor) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. Compounds of the present invention may be administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, via localized perfusion, bathing target cells directly, or by other method or any combination of the foregoing as would be known to one of ordinary skill in the art (see, for example, Remington's Pharmaceutical Sciences, 1990). In particular embodiments, the composition may be formulated for oral delivery. Pharmaceutical compositions comprising a compound of the present invention are also contemplated, and such compositions may be adapted for administration via any method known to those of skill in the art, such as the methods described above.

In particular embodiments, the composition is administered to a subject using a drug delivery device. Any drug delivery device is contemplated for use in delivering a pharmaceutically effective amount of a Wnt protein production inhibitor.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will typically determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent, for example. The administration could be intraoperative or post-operative.

In certain embodiments, pharmaceutical compositions may comprise, for example, at least about 0.1% of a Wnt protein production inhibitor. In other embodiments, the Wnt protein production inhibitor may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The Wnt protein production inhibitor may be formulated into a composition, such as a pharmaceutical composition, in a free base, neutral, or salt form. Pharmaceutically acceptable salts are described herein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents (e.g., glucose, lactose, or mannitol), assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Sterile injectable solutions may be prepared by incorporating a compound of the present invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

VI. Combination Therapy

In order to enhance or increase the effectiveness of a Wnt protein production inhibitor of the present invention, the inhibitor may be combined with another therapy, such as another agent that combats and/or prevents cancer, osteopetrosis, a degenerative disease, or type II diabetes. For example, Wnt protein production inhibitors of the present invention may be provided in a combined amount with an effective amount another agent that is known to reduce tumor size.

It is contemplated that combination therapy of the present invention may be used in vitro or in vivo. These processes may involve administering the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a Wnt protein production inhibitor is "A" and a second agent, such as an anti-cancer agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

A. Anti-Cancer Therapy

An anti-cancer agent may be used in combination therapy with Wnt protein production inhibitors of the present invention. As used herein, an "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing tumor size, inhibiting tumor growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents are well-known in the art and include, for example, chemotherapy agents (chemotherapy), radiotherapy agents (radiotherapy), a surgical procedure, immune therapy agents (immunotherapy), genetic therapy agents (gene therapy), hormonal therapy, other biological agents (biotherapy), and/or alternative therapies.

B. Osteopetrosis Therapy

Osteopetrosis, also known as marble bone disease and Albers-Schonberg disease, is an extremely rare inherited disorder whereby the bones harden, becoming denser, in contrast to the more prevalent osteomalacia, in which the bones soften. Bone marrow transplant therapy may be combined with administration of Wnt protein production inhibitors of the present invention to treat or prevent osteopetrosis. Other treatments targeting osteopetrosis that may be combined with Wnt protein production inhibitors described herein include those disclosed in the following documents, each of which is incorporated herein by reference: U.S. Pat. Nos. 7,241,732; 7,186,683; 6,943,151; 6,833,354; 6,699,873; 6,686,148; 5,806,529; 5,777,193; RE35,694; 5,641,747; and 4,843,063.

C. Degenerative Disease Therapy

As discussed herein, degenerative diseases may be treated using Wnt protein production inhibitors of the present invention. Accordingly, other treatments that target degenerative diseases may be combined with administration of the Wnt protein production inhibitors. Non-limiting examples of degenerative diseases include type II diabetes and age-related impairment of tissue repair.

1. Type II Diabetes Therapy

Type II diabetes is a chronic, progressive disease that has no clearly established cure. It is a metabolic disorder that is primarily characterized by insulin resistance, relative insulin deficiency and hyperglycemia. Treatment options that may be combined with Wnt protein production inhibitor administration include exercise, diet management to control the intake of glucose, and use of anti-diabetic drugs (e.g., metformin, phenformin, repaglinide, nateglinide, rosiglitazone, pioglitazone or miglitol).

2. Age-related Impairment of Tissue Repair Therapy

A variety of tissues degenerate over time as one ages, such as skeletal muscle and organ tissues (e.g., heart, kidney, lung and liver). Wnt protein production inhibition has been implicated in, for example, muscle regeneration (Brack et al., 2007). Therapies pertaining to age-related impairment of tissue repair that may be combined with Wnt protein production inhibitor administration include, for example, gene therapy, such as described by Barton-Davis et al. (1998; incorporated herein by reference) and drugs described by Lynch (2004; incorporated herein by reference).

VII. Examples

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

General: All chemical reactions were performed in glassware under a positive pressure of argon. The normal-phase flash column chromatography was performed with EMD silica gel 60 (230-400 mesh ASTM). TLC analyses were performed on EMD 250 μm Silica Gel 60 $F_{254}$ plates and visualized by quenching of UV fluorescence ($\lambda_{max}$=254 nm), or by staining ceric ammonium molybdate. $^1$H and $^{13}$C NMR spectra were recorded on Varian Inova-400. Chemical shifts for $^1$H and $^{13}$C NMR spectra are reported in ppm (δ) relative to the $^1$H and $^{13}$C signals in the solvent (CDCl$_3$: δ 7.26, 77.16 ppm; DMSO-d6: δ 2.50, 39.52 ppm) and the multiplicities are presented as follows: s=singlet, d=doublet, t=triplet, m=multiplet. Mass spectra were acquired on Agilent 6120 Single Quadrupole LC/MS. Analytic HPLC was performed using an Eclipse XDB-C18 5 μm column with dimension 4.6×150 mm using an Alltech 3300 evaporative light scattering detector. The purity of all compounds for biologically assays was determined to be >95% by HPLC.

Metabolic Assay Protocols:

S9 Metabolism Assay: Male ICR/CD-1 mouse S9 fractions were purchased from Celsis/In Vitro Technologies (Baltimore, Md.). 50 μL (1 mg) of S9 protein was added to a 15 mL glass screw cap tube. 700 μL of a 50 mM Tris, pH 7.5 solution, containing the compound of interest was added on ice. The final concentration of compound after addition of all reagents was 2 μM. 250 μL of an NADPH-regenerating system (1.7 mg/mL NADP, 7.8 mg/mL glucose-6-phosphate, 6 U/mL glucose-6-phosphate dehydrogenase in 2% w/v NaHCO$_3$/10 mM MgCl$_2$) was added and the tube placed in a 37° C. shaking water bath. At varying time points after addition of phase I cofactors, the reaction was stopped by the addition of 1 mL of methanol containing an internal standard compound, n-benzylbenzamide, and formic acid. The samples were incubated 10 min at room temperature and then spun once at 975×g in the glass tube. The supernatant was spun a second time at 16,000×g for 5 min in a microcentrifuge. The supernatant was analyzed by LC-MS/MS. Analytical methods were developed for each compound using an AB SCIEX 3200-QTrap, a combination triple quadrupole/ion trap instrument. Compound transitions utilized for quantitation were as follows: IWP-L6 (27): 473.2 to 303.1; aniline: 171.2 to 127.0; n-benzylbenzamide (internal standard): 212.1 to 91.1. A Shimadzu (Columbia, Md.) Prominence LC with Agilent C18 XDB column (5 micron, 50×4.6 mm) was used for chromatography. The peak areas for IWP-L6 and the aniline were normalized to the n-benzylbenzamide peak area and then the relative amount of compound present at each time point was normalized to the amount present at time 0 and presented as a percentage.

Plasma Metabolism Assay: Murine, rat, and human plasma, collected using acidified citrate dextrose (ACD) anticoagulant, were purchased from Bioreclamation (Westbury, N.Y.). IWP-L6 (27) was added to 1 mL of each plasma at a final concentration of 2 μM, the material was aliquoted into eppendorf tubes, and then incubated for the indicated time points in a 37° C. water bath. At each time point, an aliquot was removed and protein precipitated and compound extracted and analyzed as described above.

EXAMPLE 2

Results

The four IWP lead compounds (1-4) were identified in the initial screen of 200,000 compounds (ChemDiv, ChemBridge, ComGenex, Prestwick and TimTek libraries) bear similar molecular skeletons (FIG. 1). These four compounds have all been shown to suppress cell-autonomous Wnt signaling in mouse fibroblasts at low micromolar and high nanomolar concentrations (Chen, et al., 2009, which is incorporated by reference herein). The phthalazinone moiety of IWP-1 (1) and pyrimidinone moiety of IWP-2-4 (2-4) can be considered to be exchangeable scaffolding motifs for the compounds. The benzothiazole moiety appears to be a conserved motif and the phenyl group tolerates both electronic and steric perturbations.

Figure 2:
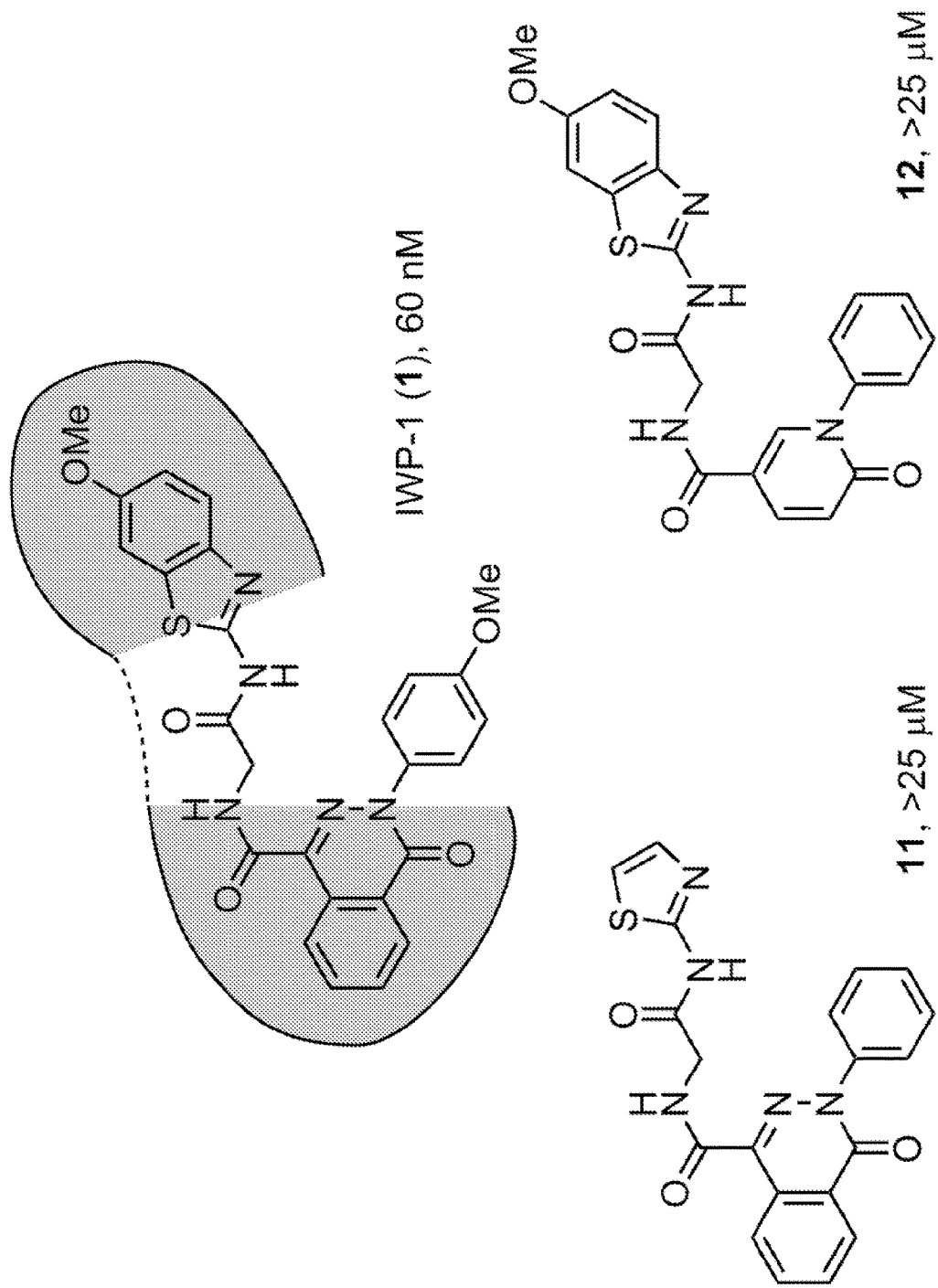
FIG. 2—The phthalazinone/pyrimidinone and the benzothiazole moieties of IWPs are important for their binding to Porcn. Shown at the top are the interactions of those two moieties with the binding pocket of the Porcn protein. At the bottom, two inhibitors which truncate some of the functionality of the moieties are shown with much lower affinities due to the weakened interaction between protein and the inhibitor.

An additional 13 Porcn inhibitors from the same screen that netted IWP-1-4 (1-4) have been identified (Dodge, et al., 2012, which is incorporate by reference herein). Five of them (6-10 which are shown in Table 1) possess similar molecular skeletons as the original IWP-1-4 (1-4) and provided additional structure-activity relationship information for further development. The discovery of 6-10 as active Porcn inhibitors confirmed that the phthalazinone and pyrimidinone moieties are scaffolding motifs. Most importantly, the phenyl and benzothiazole groups of IWP-1-4 (1-4) can be replaced by an alkyl group and a simple aromatic group, respectively. Without being bound by theory, IWPs are hypothesized to bind to Porcn by fitting the phthalazinone/pyrimidinone and the benzothiazole regions into the protein binding pocket (FIG. 2).

TABLE 1

Effects of the Substituent Groups of the Phenyl and Benzothiazole Groups of IWP-1 (1) and IWP-2 (2)[a]

A

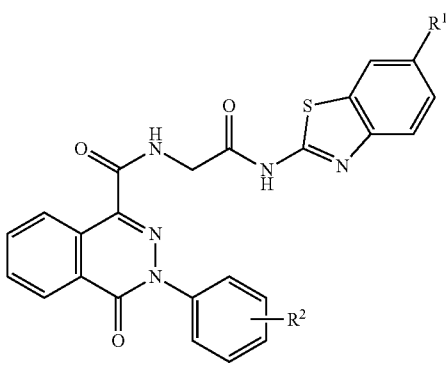

B

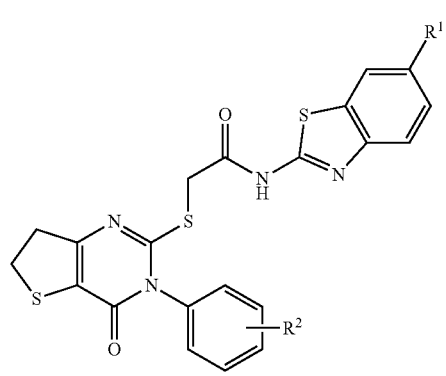

| Entry | R[1] | Scaffold | R[2] H | p-F | o-OMe | p-OMe |
|---|---|---|---|---|---|---|
| 1 | OMe | A | 210 | 90 | 90 | 60 |
| 2 |  | B | 40 | 250 | 50 | 120 |
| 3 | Me | A | 35 | 100 |  | 25 |
| 4 |  | B | 30 | 40 | 30 |  |
| 5 | H | A | 2600 | >25000 | 10000 | 25000 |
| 6 | F | A | 470 |  |  |  |
| 7 | Cl | A | 30 | 25 |  | 15 |
| 8 |  | B | 40 | 175 | 50 | 35 |
| 9 | CF$_3$ | A | 110 | 90 |  |  |
| 10 |  | B | 40 | 100 | 30 | 100 |
| 11 | NO$_2$ | A | 240 |  |  |  |
| 12 | COOEt | A | >25000 |  |  |  |

[a]EC$_{50}$ values in nM.

Figure 3:
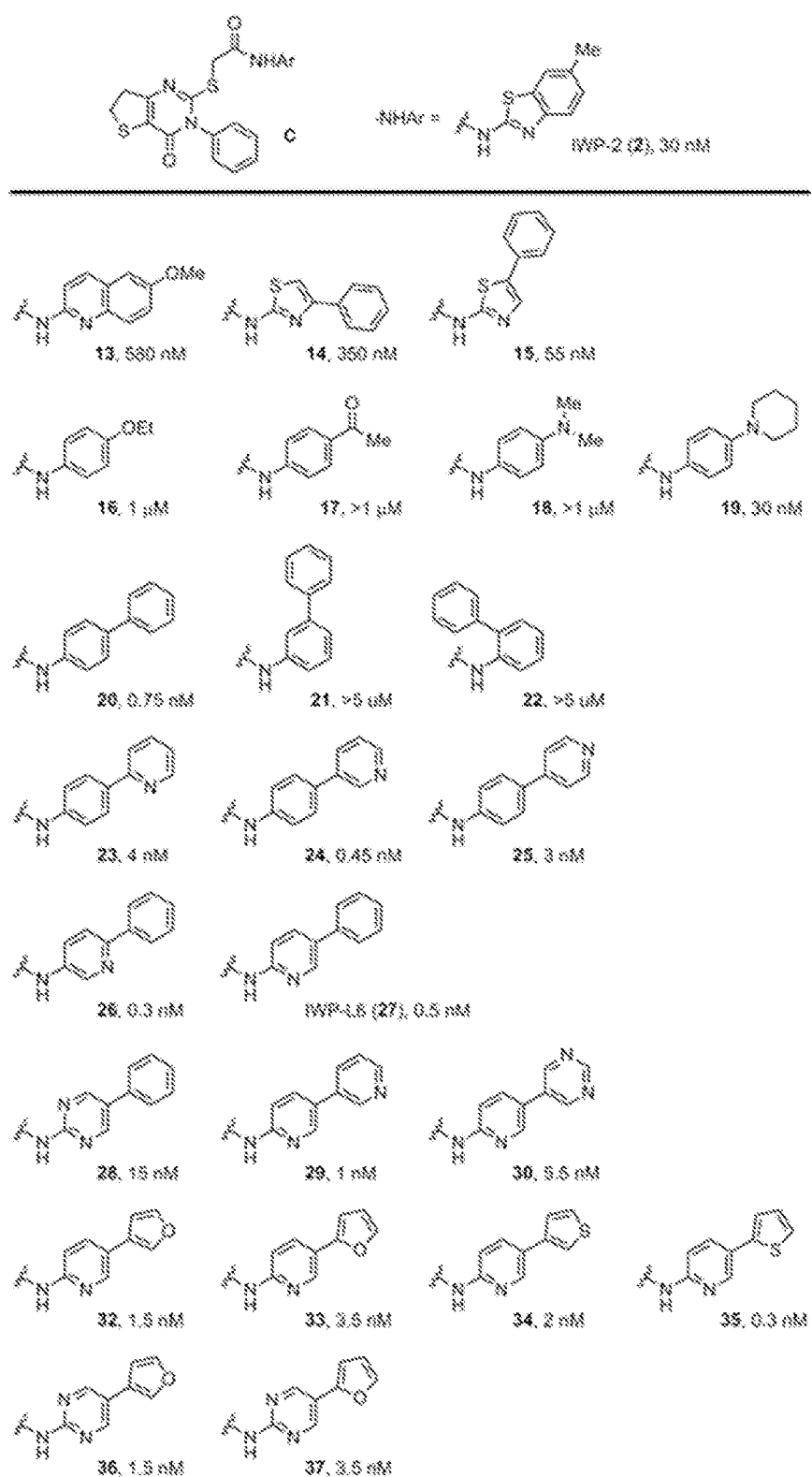
FIG. 3—Effects of the arylamide groups on the Porcn-inhibiting activity.

Motivated by the Porcn-inhibiting activities associated with earlier IWP drug candidates developed, the benzothiazole group was systematically replaced with other aromatic groups and examined the activity of molecules with general structure C (FIG. 3). Compound 13 illustrated that the binding pocket would tolerate a substituent as large as a quinolone moiety despite weakened activity. The phenylthiazole derivatives (14 and 15) were also found to be active Porcn inhibitors, and the 5-phenyl derivative 15 has a similar potency as IWP-2 (2). Only weak or nearly no activity was observed with simple phenyl derivatives (16-18) that contain a small substituent group at the 4-position. However, installing a piperidine group resulted in an equal potent inhibitor (19) as IWP-2 (2). The potential of biaryl systems as new Porcn inhibitors was then explored.

During the initial screening, the 4-biphenyl derivative, 20, was 40 times more potent than IWP-2 (2) while a significant loss of activity was observed with the 3- and 2-biphenyl derivatives (21 and 22). Next, a nitrogen atom was introduced to either the outer or inner phenyl ring (23-27) and a slight improvement of activity was observed with 24, 26 and 27, which are also more soluble than IWP-2 (2) and 20. Introduction of an additional nitrogen atom (28-30) did not appear to significantly improve the activity. The phenyl group was replaced with a furan or thiophene group (32-37) and found the 2-thiophenyl derivative, 35, to be a highly potent Wnt inhibitor.

Figure 4:
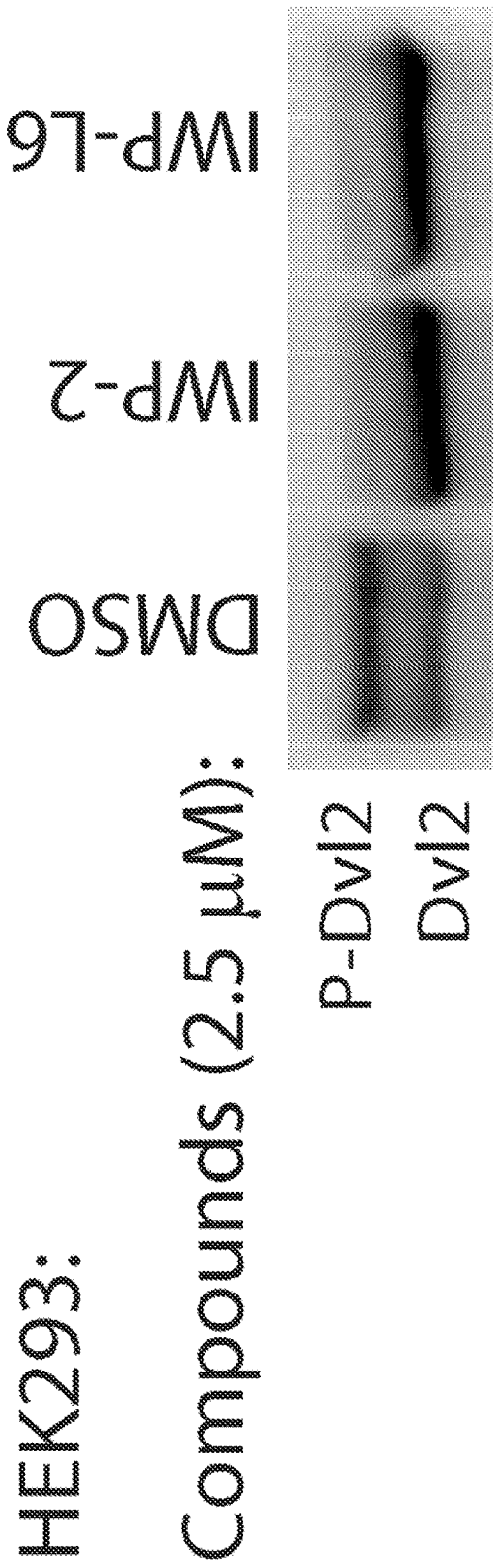
FIG. 4—The Porcn inhibitor, IWP-L6 (FIG. 3 Compound 27), blocks the phosphorylation of the cytoplasmic Wnt pathway effector Dvl2 shown through gel electrophoresis.
Figure 5:
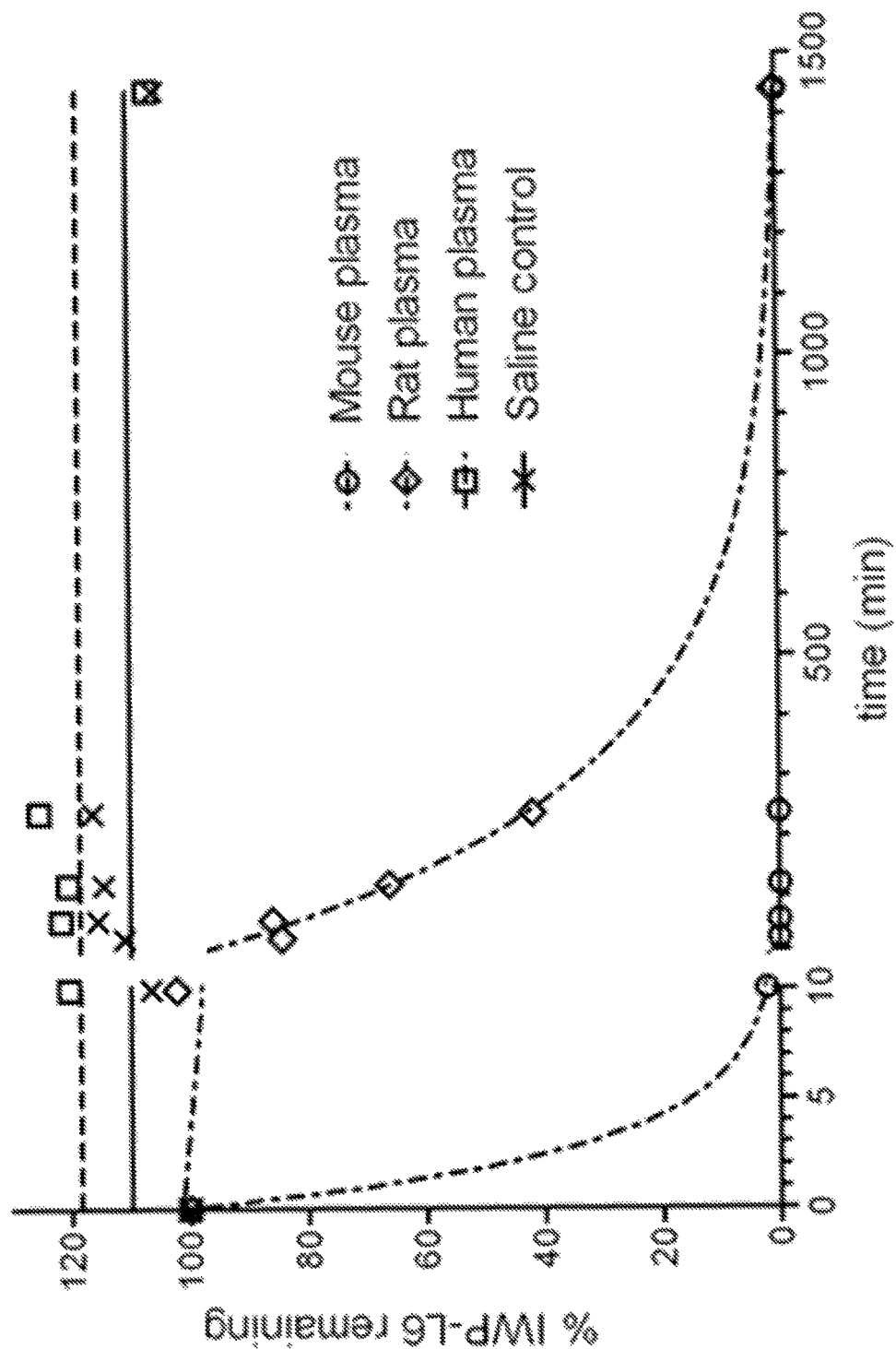
FIG. 5—Stability of IWP-L6 (FIG. 3 Compound 27) in the plasma of different animals as a function of increasing time which showed little degradation of the compound in human plasma but much more significant degradation in rat and mouse plasma.

Among the five newly identified sub-nanomolar IWPs, compound 27 was selected for further biological evaluations and named IWP-L6. IWP-L6 (27) was found to effectively suppressed the phosphorylation of dishevelled 2 (Dvl2) in HEK293 cells, a biochemical event associated with many Wnt-dependent cellular responses (FIG. 4) (Dodge, et al., 2012; Jacob, et al., 2011, which are incorporated by reference herein). The in vivo stability of IWP-L6 (27) (FIG. 5) was further profiled. Whereas IWP-L6 (27) was stable in human plasma over 24 h, the compound was rapidly metabolized in rat plasma ($t_{1/2}$=190 min), murine plasma ($t_{1/2}$=2 min), and the murine liver S9 fractions ($t_{1/2}$=26 min). The major metabolites are the amide cleavage products. Similar species-dependent metabolitic profiles due to the involvement of carboxylesterase (CES) have been reported with other drug candidates (Eng, et al., 2010; Liu, et al., 2011) These observations are consistent with the elevated activity of CES in mouse and rat but not human (Berry, et al., 2009; Rudakova, et al., 2011; Bahar, et al., 2012).

Figure 6:
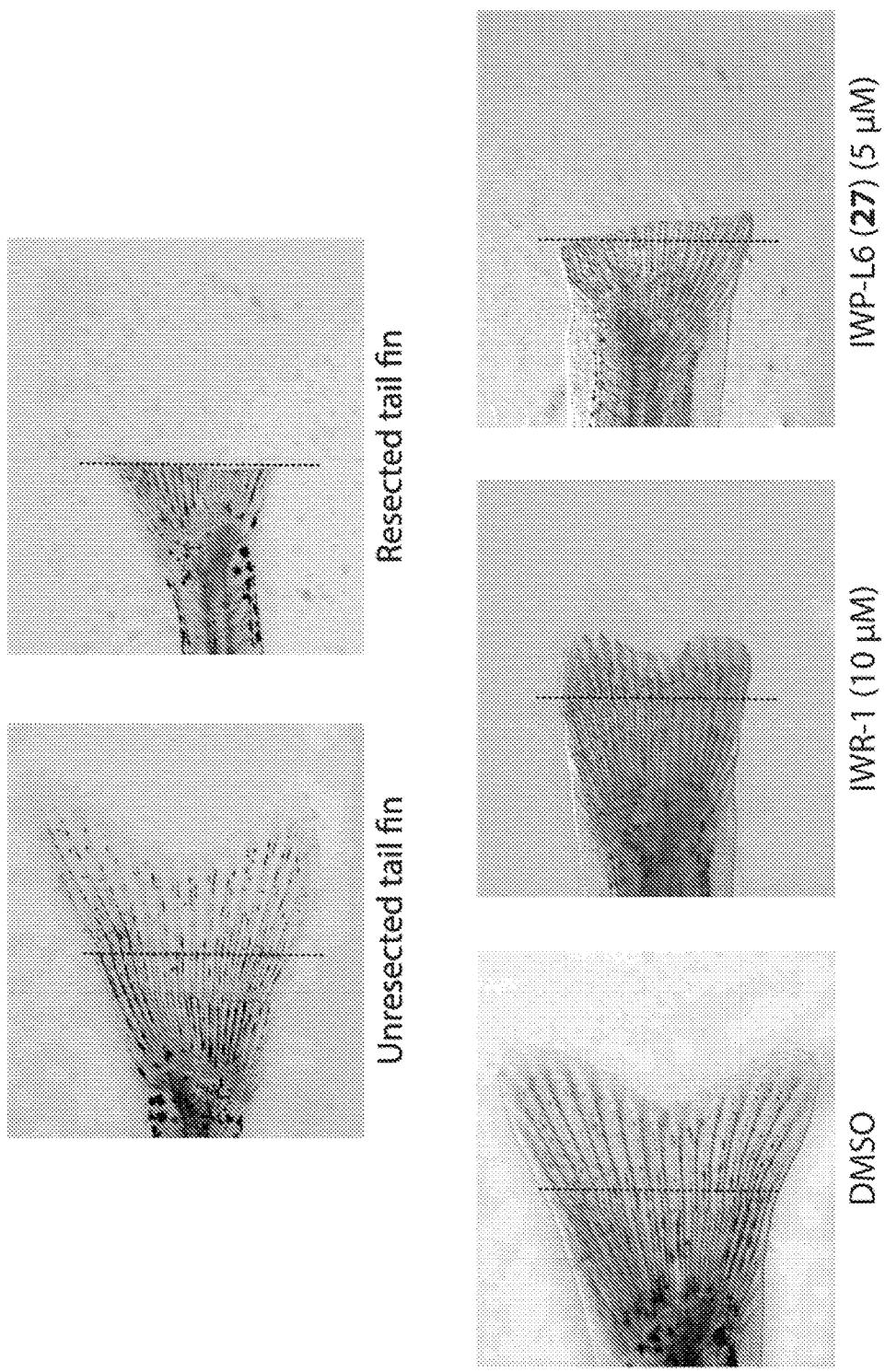
FIG. 6—The inhibition of the regeneration of the tailfin of juvenile zebrafish was shown to be more significant after treatment with IWP-L6 (FIG. 3 Compound 27) than the previous inhibitor IWP-1.
Figure 9A:
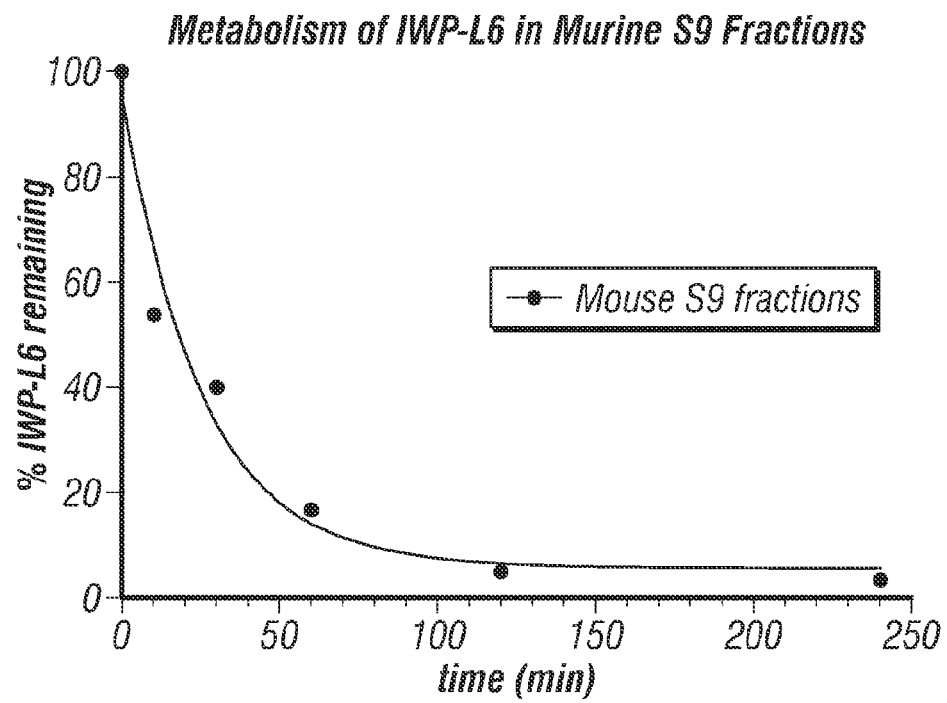
Figure 9B:
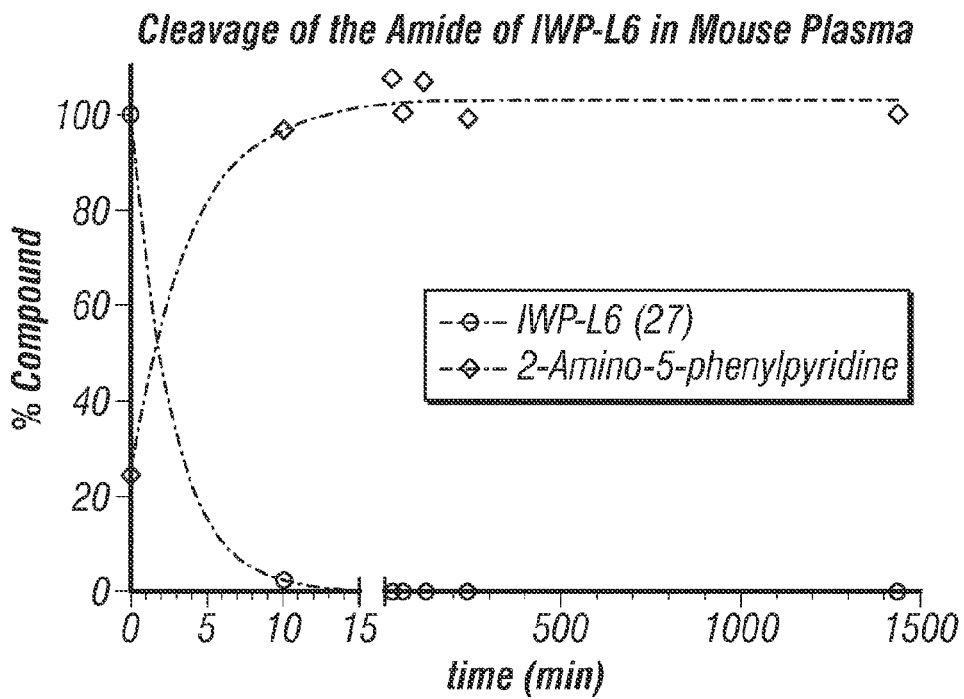
Figure 9C:
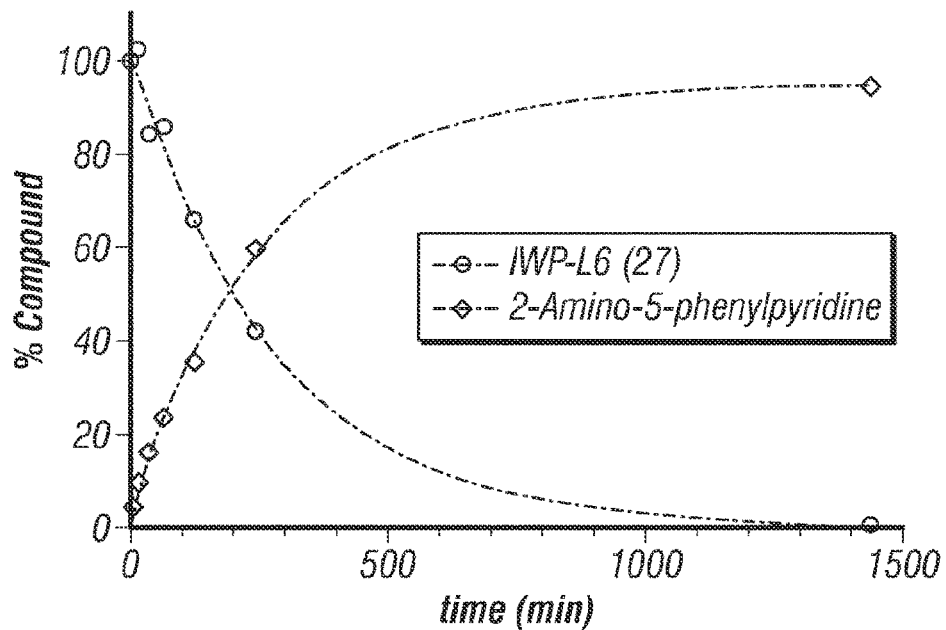
Figure 9D:
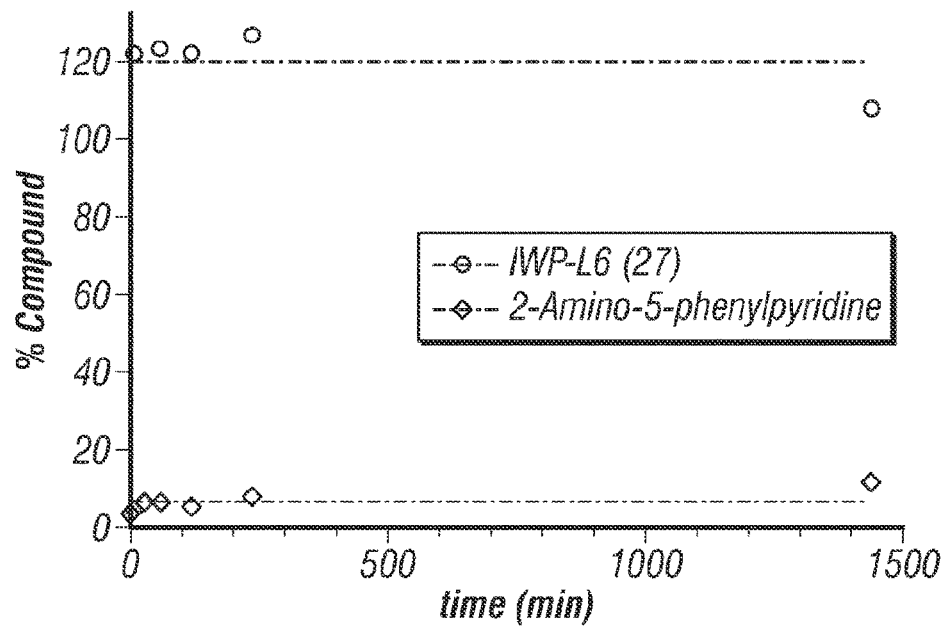
Figure 10:
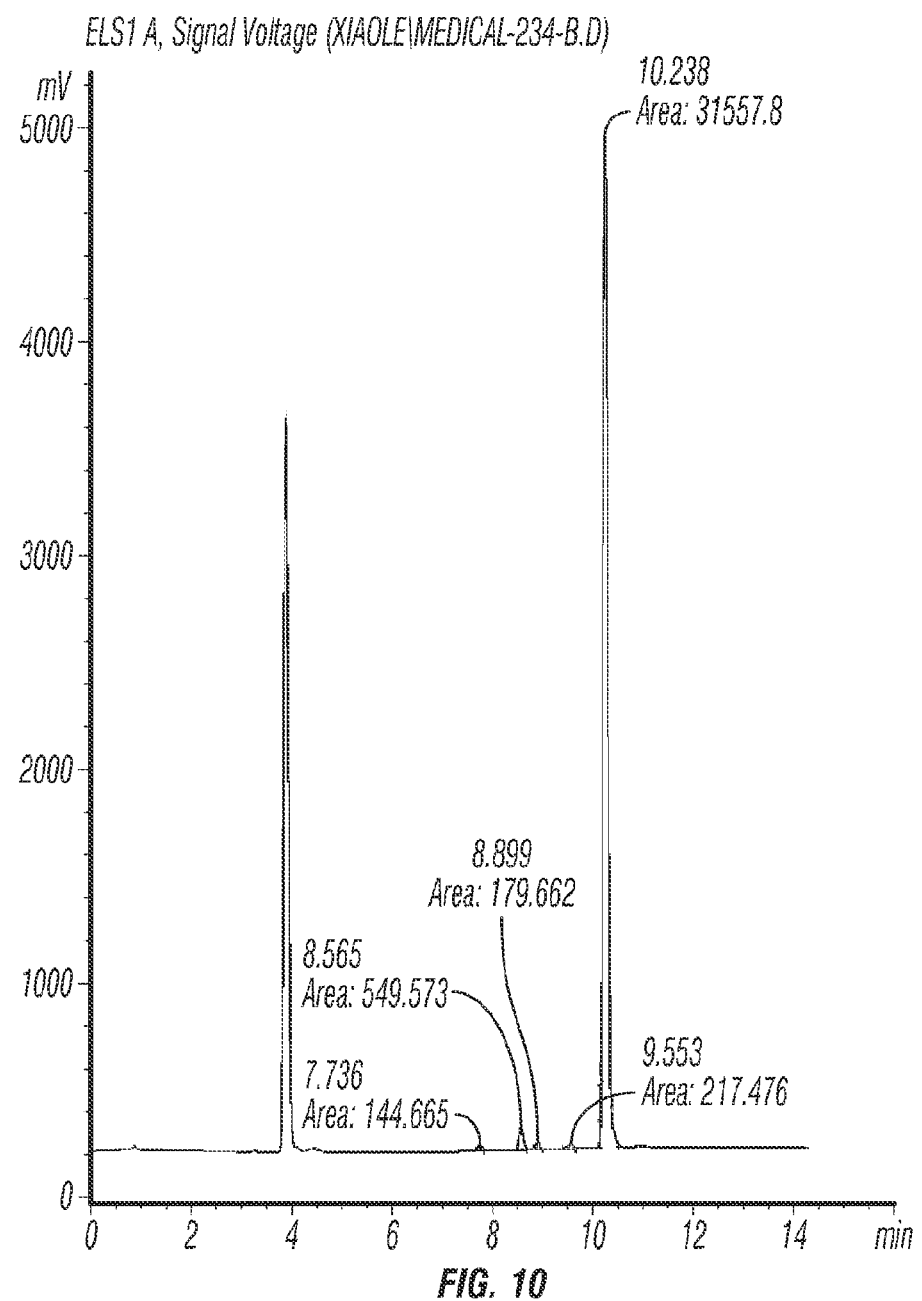
FIG. 10—HPLC trace showing the purity of the inhibitor, IWP-L6.
Figure 11A:
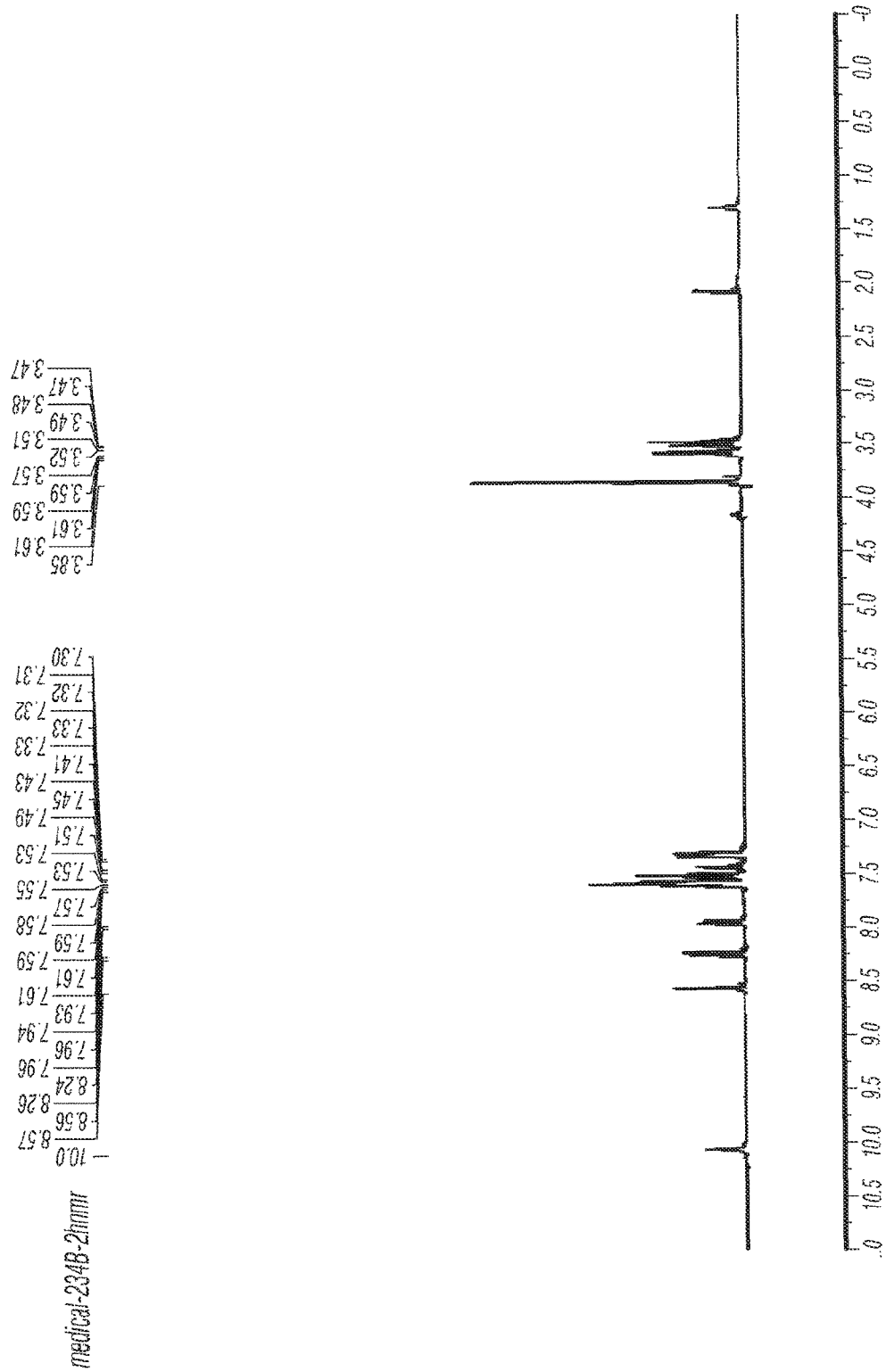
FIGS. 11A-C—(FIG. 11A) $^1$H NMR spectra for IWP-L6.
Figure 11B:
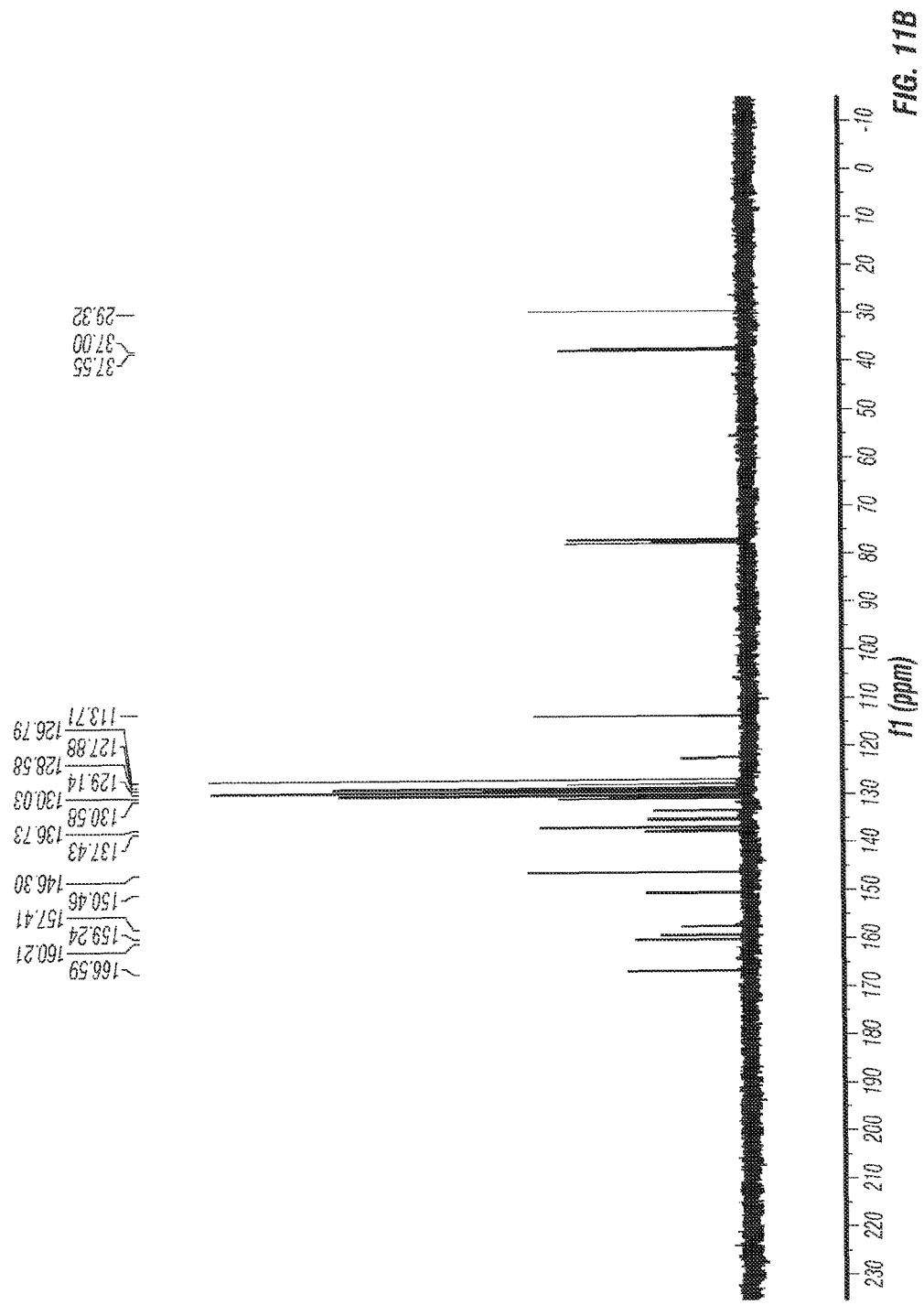
Figure 11C:
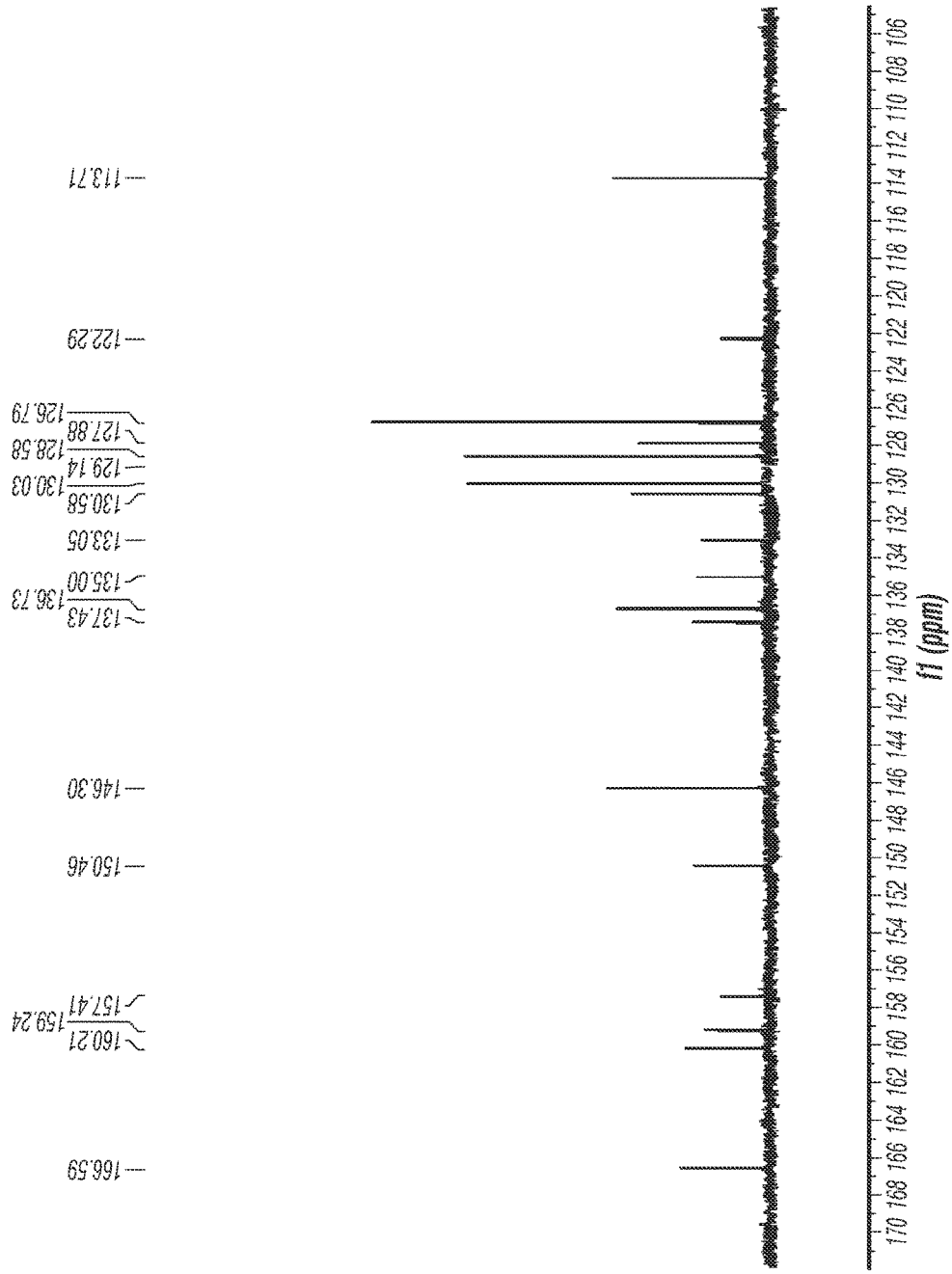

Despite its modest metabolic stability in mouse-derived plasma, IWP-L6 (27) was highly active in zebrafish. Both the tankyrase (Tnks) inhibitor IWR-1 and the Porcn inhibitor IWP-12 (7) have been previously shown to effectively block the regeneration of the tailfin, a Wnt-dependent process, in adult and juvenile fish (Chen, et al., 2009; Dodge, et al., 2012; Lu, et al., 2009, which are incorporated by reference herein). In this disclosure, IWP-L6 (27) was found to exhibit more potent activity (FIG. 6) than those two compounds. IWP-L6 (27) and 35, but not 30 and 32, were further shown to effectively inhibit posterior axis formation, a Wnt/β-catenin dependent developmental process, at low micromolar concentrations (FIG. 7). IWP-L6 (27) and 35 are therefore at least 10 times more potent than IWP-12 (7) and 2.5 times more potent than IWR-1 in this in vivo assay (Lu, et al., 2009). While there is only 69% sequence identity between mouse Porcn and zebrafish Porcn, the in vitro $EC_{50}$ values (FIG. 3) measured in mouse fibroblasts (L cells) correlate with the in vivo activity observed in fish but not linearly.

IWP2 (2) has been previously shown to specifically and reversibly block Wnt signaling and Wnt mediated branching morphogenesis in cultured mouse embryonic kidneys (Karner, et al., 2010; Dodge, et al., 2012, which are incorporated by reference herein). IWP-L6 (27) is at least 100 times more potent than IWP-2 (2) based upon these experiments. Embryonic day (E) 11.5 kidneys in media containing various doses (1 nM to 1 μM) of IWP-L6 (27) were cultured. Doses of 10 nM and above significantly reduced branching morphogenesis relative to DMSO treated controls (FIG. 8). Doses of 50 nM and above completely blocked branching morphogenesis indicating a complete inhibition of Wnt signaling. In comparison, a dose of 5 μM of IWP-2 (2) was required to obtain similar results (Dodge, et al., 2012; Karner, et al., 2010).

EXAMPLE 3

Synthesis of Inhibitors

General Synthetic Strategies: In order to prepare the inhibitors reported in this disclosure, the amine derivative of the bisphenyl compound is reacted with chloroacetyl chloride to form an amide bond. After the formation of the amide bond, the 2-chloroamide is reacted with 3-phenyl-6,7-dihydrothieno[3,2-d]pyrimidine-2-thione-4-one to generate the target inhibitor of interest. A general schematic for the synthetic process is shown below.

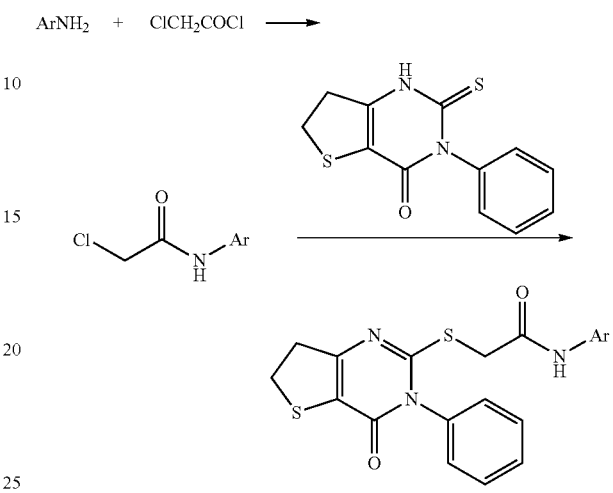

The specific synthesis of IWP-L6 is described in detail below. The specific synthesis below combined with the general synthetic schematic serves as an illustrative example of the synthesis of these inhibitors described in this disclosure. General modifications of this methodology such as those by a skilled artisan would carry out in order to optimize the yield or otherwise improve the production of the desired compound are also contemplated.

Synthesis of IWP-L6 (27): To a solution of 1,8-diazabicyclo[5.4.0]undec-7-ene (DBU, 26 mL, 0.17 mol) in methanol (90 mL) were added methyl thioglycolate (14.4 mL, 0.158 mol) and acrylonitrile (12 mL, 0.17 mol) at 0° C. The solution was stirred at 0° C. for 5 h and then at 80° C. overnight. After cooling to room temperature, the solvent was evaporated, quenched with a saturated solution of ammonium chloride, and extracted with ethyl acetate. The organic layer was dried over sodium sulfate, concentrated, and purified by silica gel column chromatography (40% ethyl acetate/hexanes) to give 3-amino-2-(methoxycarbonyl)-4,5-dihydrothiophene (9.72 g, 39%) as a yellow solid: $^1$H NMR (400 MHz, CDCl$_3$) δ 2.86 (t, J=8.0 Hz, 2H), 3.03 (t, J=8.0 Hz, 2H), 3.68 (s, 3H) (Baraldi, et al., 1995, which is incorporated by reference herein).

A solution of 3-amino-2-(methoxycarbonyl)-4,5-dihydrothiophene (1.00 g, 5.78 mmol) and phenyl isothiocyanate (937 mg, 6.94 mmol) in pyridine (18 mL) was stirred at 100° C. overnight. The solvent was then evaporated and the residue was purified by silica gel column chromatography (30% ethyl acetate/hexanes then acetone) and then washed three times with ethyl acetate to give pure 3-phenyl-6,7-dihydrothieno[3,2-d]pyrimidine-2-thione-4-one (635 mg, 42%). $^1$H NMR (400 MHz, DMSO-d$_6$) δ 13.17 (s, 1H) 7.30-7.50 (m, 3H), 7.08-7.20 (m, 2H), 3.20-3.40 (m, 4H).

To a solution of 5-phenylpyridin-2-amine (170 mg, 1.00 mmol) in benzene/THF (9/1, 10.0 mL) was added a solution of chloroacetylchloride (0.111 mL, 1.40 mmol) in benzene (1.0 mL). The reaction mixture was then stirred at 50° C. overnight. After cooling to room temperature, the solution was washed with a saturated solution of sodium bicarbonate and water, dried over sodium sulfate, and concentrated to give 2-chloro-N-(5-phenylpyridin-2-yl)acetamide, which was used directly for next step without purification.

A solution of 3-phenyl-6,7-dihydrothieno[3,2-d]pyrimidine-2-thione-4-one (81 mg, 0.310 mmol), 2-chloro-N-(5-phenylpyridin-2-yl)acetamide (80 mg, 0.325 mmol), and triethylamine (0.13 mL, 0.93 mmol) in N,N-dimethylformamide (DMF, 3.0 mL) was stirred at 80° C. for 2 h. The reaction was quenched with water, extracted with ethyl acetate, washed three times each with water and brine, dried over sodium sulfate, concentrated, and purified by silica gel column chromatography (30% ethyl acetate/hexanes) to give IWP-L6 (27) (136 mg, 93%) as white solid $^1$H NMR (400 MHz, CDCl$_3$) 10.06 (s, 1H), 8.57 (d, J=2.1 Hz, 1H), 8.25 (d, J=8.6 Hz, 1H), 7.95 (dd, J=8.6, 2.4 Hz, 1H), 7.56-7.63 (m, 5H), 7.48-7.56 (m, 2H), 7.40-7.47 (m, 1H), 7.29-7.35 (m, 2H), 3.85 (s, 2H), 3.54-3.62 (m, 2H), 3.44-3.52 (m, 2H); $^{13}$C NMR (100 MHz, CDCl$_3$) δ 166.6, 160.2, 159.2, 157.4, 150.5, 146.3, 137.4, 136.7, 135.0, 133.0, 130.6, 130.0, 129.1, 128.6, 127.9, 126.8, 122.3, 113.7, 37.6, 37.0, 29.3. MS(ES)$^+$ calcd for C$_{25}$H$_{21}$N$_4$O$_2$S$_2$ (M+H)$^+$ 473.1, found 473.1.

* * *

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

U.S. Pat. No. 4,843,063
U.S. Pat. No. 5,641,747
U.S. Pat. No. 5,777,193
U.S. Pat. No. 5,806,529
U.S. Pat. No. 6,686,148
U.S. Pat. No. 6,699,873
U.S. Pat. No. 6,833,354
U.S. Pat. No. 6,943,151
U.S. Pat. No. 7,186,683
U.S. Pat. No. 7,241,732
U.S. Pat. RE35,694
Ailles and Weissman, *Curr. Opin. Biotech.*, 18:460-466, 2007.
Angers and Moon, *Nature Rev.*, 10:468-477, 2009.
Bahar et al., *J. Pharma. Sci.*, 101:3979-3988, 2012.
Baraldi et al., *J. Org. Chem.*, 60:1461-1463, 1995.
Barker and Clevers, *Nat. Rev. Drug Discov.*, 5:997-1014, 2006.
Barton-Davis et al., *Proc. Natl. Acad. Sci. USA*, 95:15603, 1998.
Berry et al., *Drug. Metab. Lett.*, 3:70-77, 2009.
Brack et al., *Science*, 317:807-810, 2007.
Chen et al., *J. Cell Sci.* 2012 (Epub ahead of print)
Chen et al., *Nat. Chem. Biol.*, 5:100-107 2009.
Chen et al., *Oncogene*, 27:3483-3488, 2008.
Clevers, *Cell*, 127:469-480, 2006.
Clevers and Nusse, *Cell*, 149:1192-1205, 2012.
Dodge et al., *J. Biol. Chem.*, 287:23246-23254, 2012.
Eng et al., *Xenobiotica*, 40:369-380, 2010.
Greene and Wuts, In: *Protective Groups in Organic Synthesis*, 2$^{nd}$ Ed.; Wiley, NY, 1999.
Handbook of Pharmaceutical Salts: Properties, Selection and Use, Stahl & Wermuth (Eds.), Verlag Helvetica Chimica Acta, 2002.
Huang and He, *Curr. Opin. Cell Biol.*, 20(2):119-125, 2008.
Huang et al., *Nature*, 461:614-620, 2009.
Jacob et al., *Sci. Signal.*, 4(157):ra4, 2011.
Kamer, et al., *Dev. Dyn.*, 239:2014-2023, 2010.
Liu et al., *Science*, 317:803-806, 2007.
Liu et al., *Drug Metab. Dispos.*, 39:1840-1849, 2011.
Lu, et al., *Bioorg. Med. Chem. Lett.*, 19:3825-3827, 2009.
Lum and Clevers, *Science*, 337:922-923, 2012.
Lynch, *Exp. Opin. Emerging Drugs*, 9:345, 2004.
March's Advanced Organic Chemistry: Reactions, Mechanisms, and Structure (March's Advanced Organic Chemistry), Smith and March (Eds.), 2007.
Moro et al., *Dev. Biol.*, 366:327-340, 2012.
Polakis, *Curr. Opin. Genet. Develop.*, 17:45-51, 2007.
Proffitt et al., *Cancer Res.*, 73:502-507, 2013.
Remington's Pharmaceutical Sciences, 18$^{th}$ Ed. Mack Printing Company, 1289-1329, 1990.
Ren et al., *J. Mol. Cell Cardiol.*, 51:280-287, 2011.
Reya and Clevers, *Nature*, 434:843-850, 2005.
Rudakova et al., *Bull. Exp. Biol. Med.*, 152:73-75, 2011.
Sato et al., *Nature*, 469:415-418, 2011.
Sjoblom et al., *Science*, 314:268-274, 2006.
ten Berge et al., *Nat. Cell Biol.*, 13:1070-1075, 2011.
van Amerongen and Nusse, *Development*, 136, 3205-3214, 2009.
Veeman et al., *Developmental Cell*, 5:367, 2003.
Yang et al., *Cell*, 132:387-396, 2008.

The invention claimed is:

1. A compound of the formula:

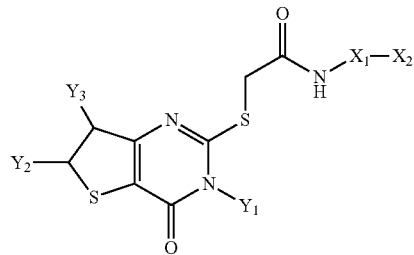

wherein:
X$_1$ is arenediyl$_{(C\leq 8)}$, heteroarenediyl$_{(C\leq 8)}$ or a substituted version of any of these groups;
X$_2$ is aryl$_{(C\leq 8)}$, heteroaryl$_{(C\leq 8)}$, or a substituted version of any of these groups;
Y$_1$ is alkyl$_{(C\leq 8)}$, aryl$_{(C\leq 8)}$, or a substituted version of any of these groups;
Y$_2$ or Y$_3$ are each independently hydrogen, halo, hydroxy, alkoxy$_{(C\leq 8)}$, alkyl$_{(C\leq 8)}$, or a substituted version of any of these groups; or a pharmaceutically acceptable salt or tautomer thereof.

2. The compound according to claim 1, wherein X$_1$ is of the structure:

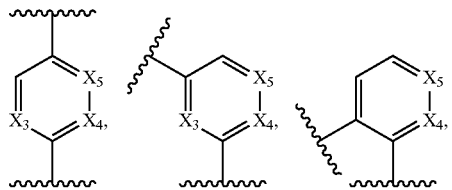

wherein:

$X_3$, $X_4$, or $X_5$ are each independently CH or N;
or a substituted version of any of these groups.

3. The compound according to claim 1, wherein $X_1$ is of the structure:

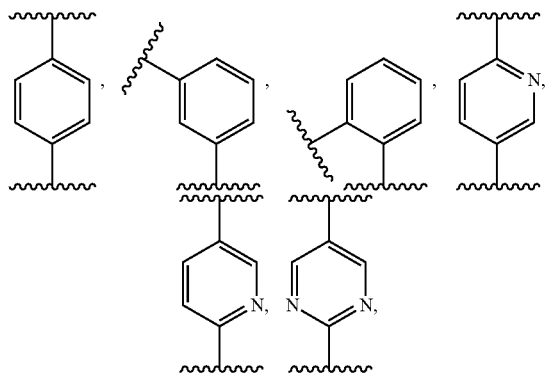

or a substituted version of any of these groups.

4. The compound according to claim 1, wherein $X_1$ is of the structure:

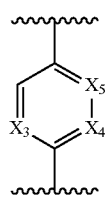

wherein:

$X_3$, $X_4$, or $X_5$ are each independently CH or N;
or a substituted version of this group.

5. The compound according to claim 1, wherein $X_1$ is of the structure:

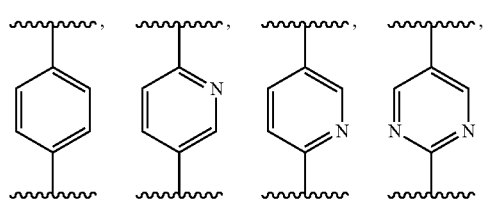

or a substituted version of any of these groups.

6. The compound according to claim 1, wherein $X_1$ is not substituted.

7. The compound according to claim 1, wherein $X_2$ is aryl$_{(C≤8)}$ or a substituted aryl$_{(C≤8)}$.

8. The compound according to claim 1, wherein $X_2$ is heteroaryl$_{(C≤8)}$ or a substituted heteroaryl$_{(C≤8)}$.

9. The compound according to claim 1, wherein $X_2$ is phenyl or a substituted version of this group.

10. The compound according to claim 1, wherein $X_2$ is pyridinyl, pyrimidinyl, furanyl, thienyl or a substituted version of any of these groups.

11. The compound according to claim 10, wherein $X_2$ is 2-pyridinyl, 3-pyridinyl, 4-pyridinyl, 5-pyrimidinyl, 2-furanyl, 3-furanyl, 2-thienyl, 3-thienyl, or a substituted version of any of these groups.

12. The compound according to claim 1, wherein $X_2$ is not substituted.

13. The compound according to claim 1, wherein the compound is:

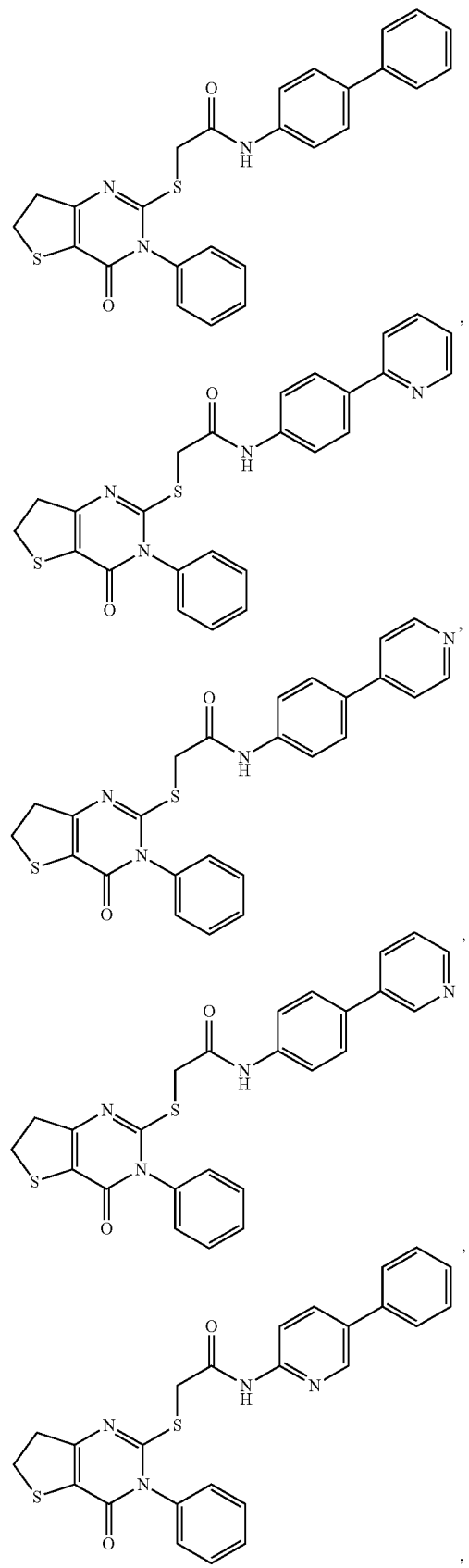

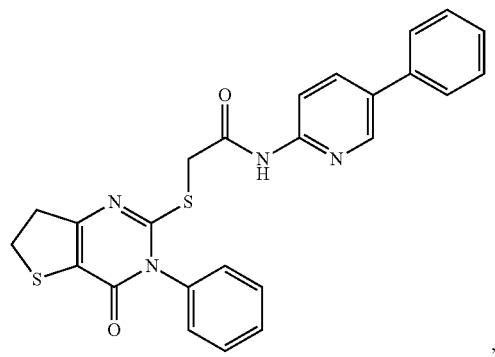
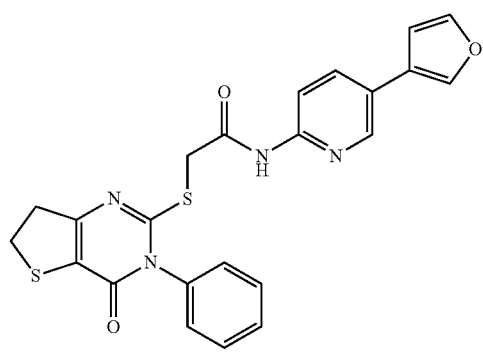
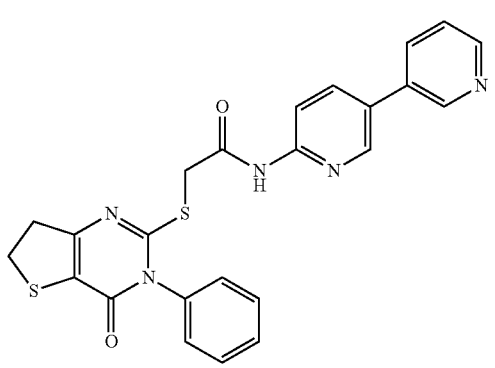
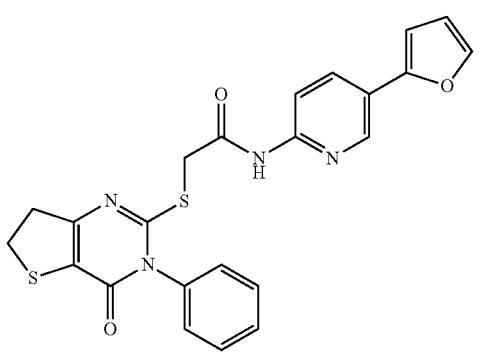
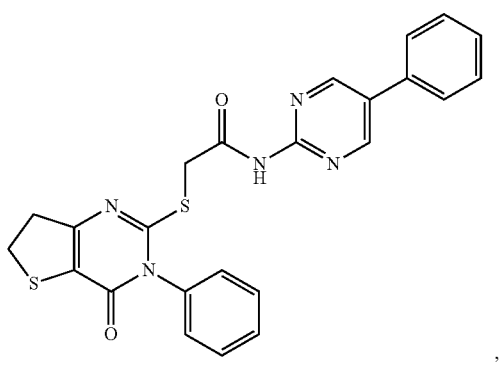
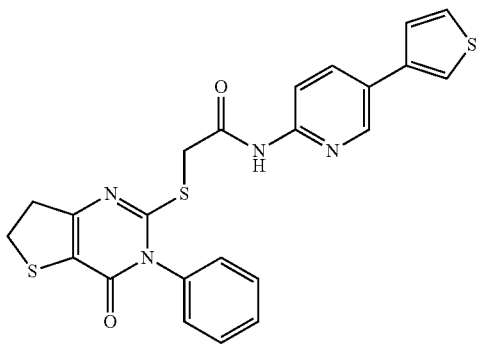
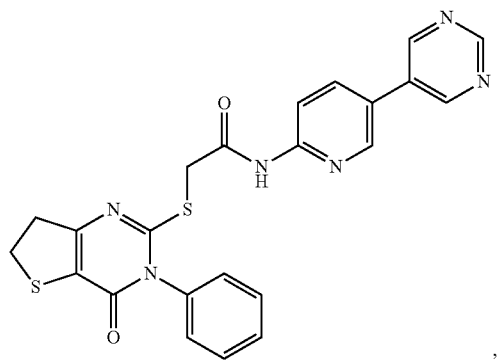
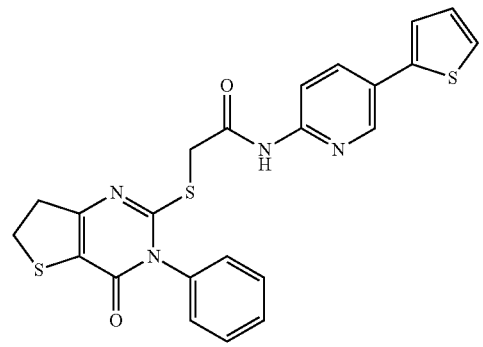

-continued
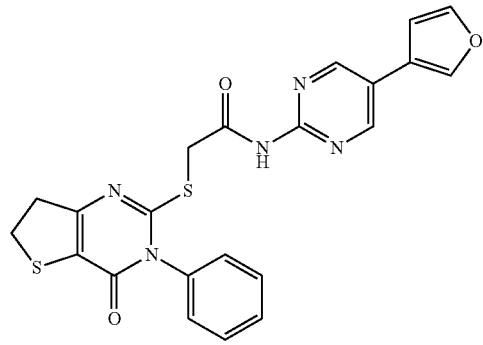
,
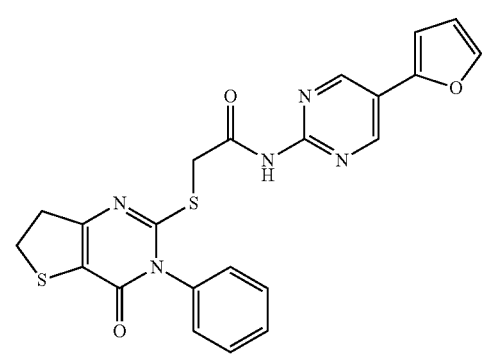
,
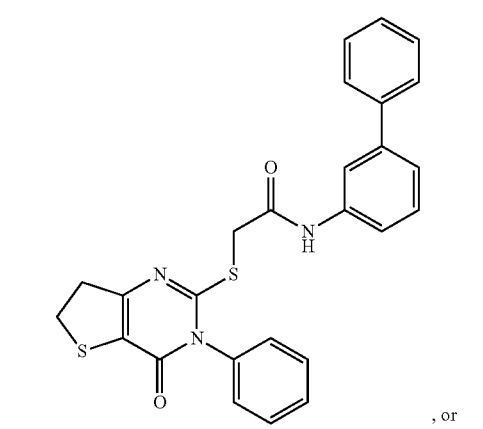
, or
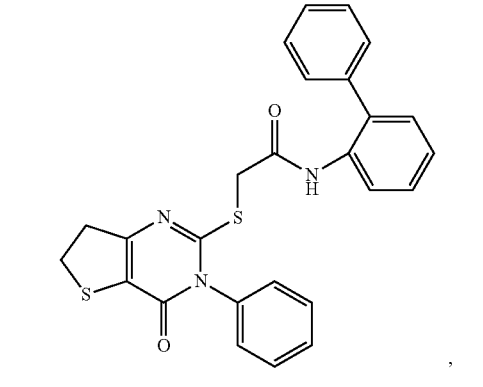 [SMILES: O=C(CSc1nc2c(c(=O)n1-c1ccccc1)SCC2)Nc1ccccc1-c1ccccc1]
,
or a pharmaceutically acceptable salt or tautomer thereof.
14. The compound of claim 13, further defined as:
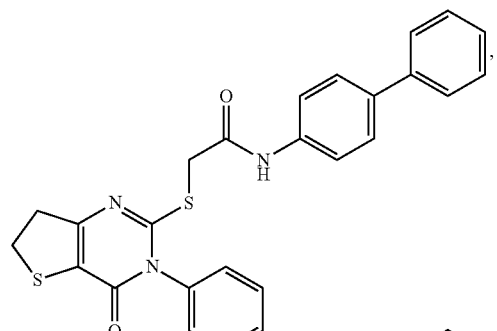
,
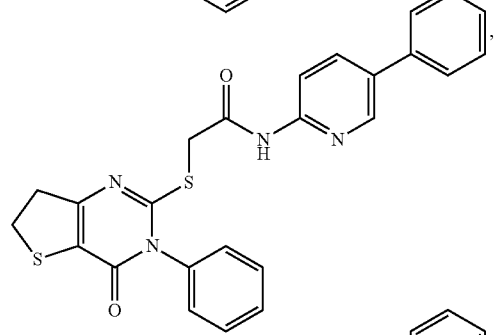
,
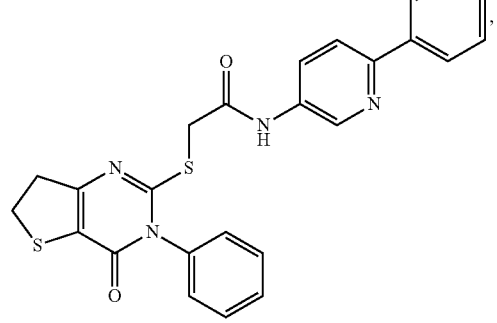
,
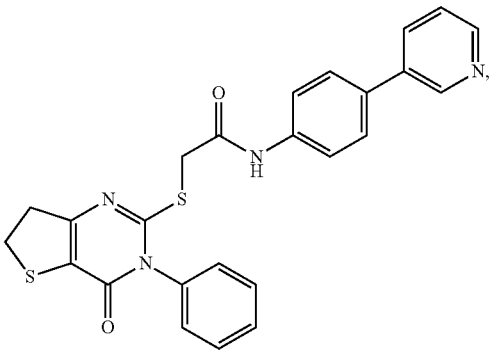
, or
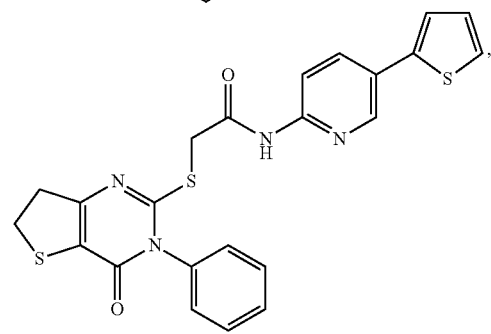
,
or a pharmaceutically acceptable salt or tautomer thereof.

15. A method of inhibiting a Wnt protein signaling in a cell comprising administering to the cell an effective amount of a compound according to claim 1.

16. The compound of claim 1, wherein $Y_1$ is $aryl_{(C \leq 8)}$.

17. The compound of claim 16, wherein $Y_1$ is phenyl.

18. The compound according to claim 17, wherein $Y_2$ and $Y_3$ are hydrogen.

19. A pharmaceutical composition comprising a pharmaceutically acceptable carrier, diluent, and/or excipient and a compound according to claim 1.

* * * * *